(12) United States Patent
Koide et al.

(10) Patent No.: US 8,419,627 B2
(45) Date of Patent: Apr. 16, 2013

(54) TRANSMITTING/RECEIVING SYSTEM AND MEDICAL SYSTEM

(75) Inventors: Naoto Koide, Tokyo (JP); Masatoshi Homan, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1147 days.

(21) Appl. No.: 12/343,826

(22) Filed: Dec. 24, 2008

(65) Prior Publication Data

US 2009/0163772 A1 Jun. 25, 2009

(30) Foreign Application Priority Data

Dec. 25, 2007 (JP) ................. 2007-332936

(51) Int. Cl.
*A61B 1/06* (2006.01)

(52) U.S. Cl.
USPC ........................................... 600/160

(58) Field of Classification Search .......... 600/103, 600/109, 117, 118, 160, 178
See application file for complete search history.

(56) References Cited

U.S. PATENT DOCUMENTS

| | | | |
|---|---|---|---|
| 5,604,531 A | 2/1997 | Iddan et al. | |
| 6,099,482 A * | 8/2000 | Brune et al. | 600/549 |
| 2005/0222490 A1* | 10/2005 | Glukhovsky et al. | 600/102 |
| 2006/0002495 A1* | 1/2006 | Shirakawa et al. | 375/345 |
| 2006/0154628 A1* | 7/2006 | Mochizuki | 455/134 |
| 2007/0066259 A1* | 3/2007 | Ryan et al. | 455/234.1 |
| 2008/0114224 A1* | 5/2008 | Bandy et al. | 600/302 |
| 2008/0158076 A1* | 7/2008 | Walley | 343/745 |
| 2008/0161660 A1* | 7/2008 | Arneson et al. | 600/302 |
| 2008/0193139 A1* | 8/2008 | Bettesh | 398/128 |
| 2009/0076320 A1 | 3/2009 | Shigemori | |
| 2010/0016661 A1* | 1/2010 | Nagase et al. | 600/109 |

FOREIGN PATENT DOCUMENTS

| | | |
|---|---|---|
| EP | 0 667 115 A1 | 8/1995 |
| EP | 1 867 280 A1 | 12/2007 |
| JP | 2004-310402 | 11/2004 |
| JP | 2005-319097 | 11/2005 |
| JP | 2006-296971 | 11/2006 |
| JP | 2007-049730 | 2/2007 |

OTHER PUBLICATIONS

Japanese Office action dated Sep. 25, 2012 from corresponding Japanese Patent Application No. JP 2007-332936, together with an English language translation.

* cited by examiner

*Primary Examiner* — Philip R Smith
(74) *Attorney, Agent, or Firm* — Scully Scott Murphy & Presser, PC

(57) ABSTRACT

A transmitting/receiving system includes a transmitting apparatus that generate modulated signals each containing a broadband signal component and a narrowband signal component, and transmits the modulated signals to the outside; and a receiving device that receives the modulated signals via at least three receiving antennas. The receiving device includes a signal processing system that processes the broadband signal component contained in the modulated signal; and a received-strength detecting system that processes the narrowband signal component contained in the modulated signal.

11 Claims, 13 Drawing Sheets

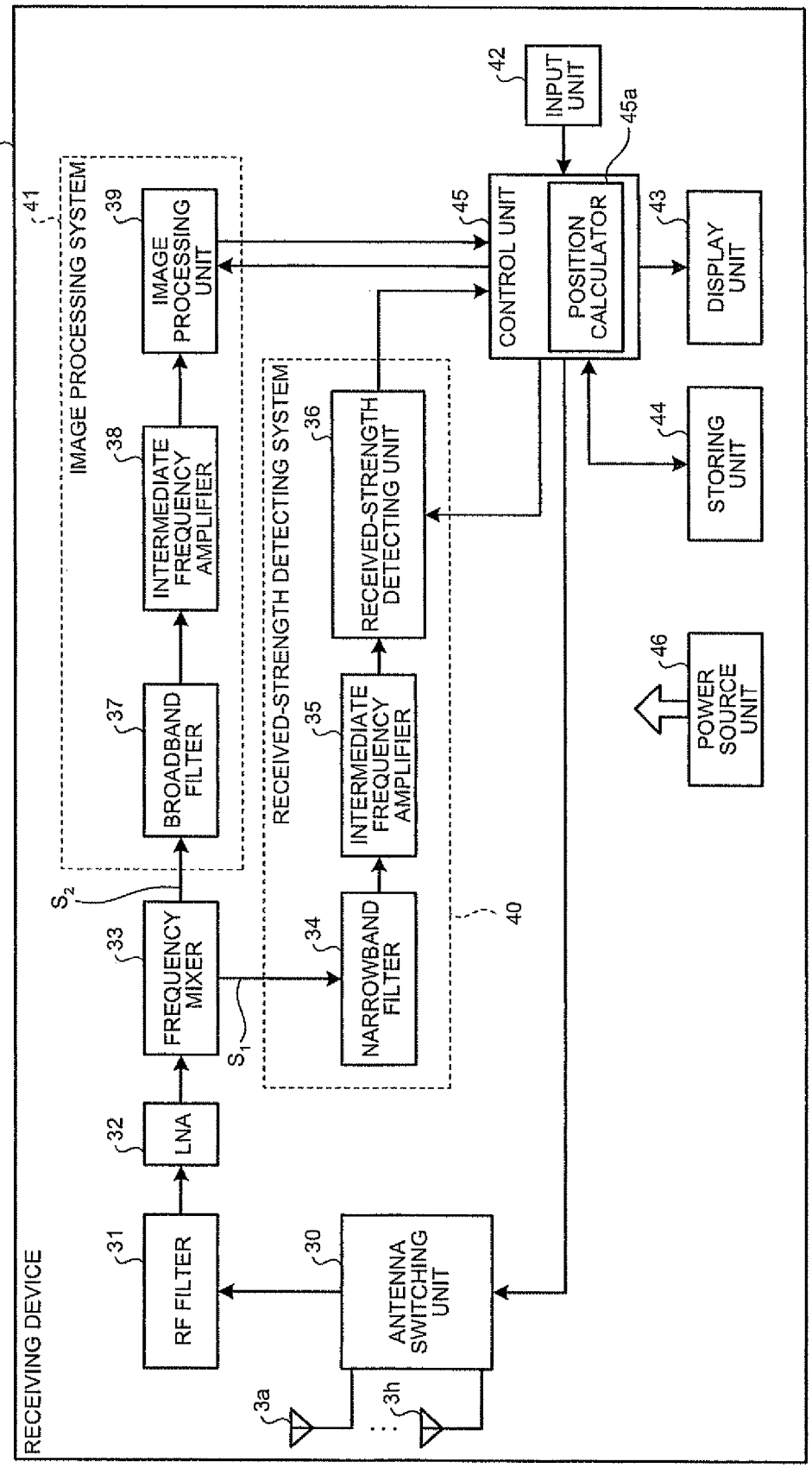

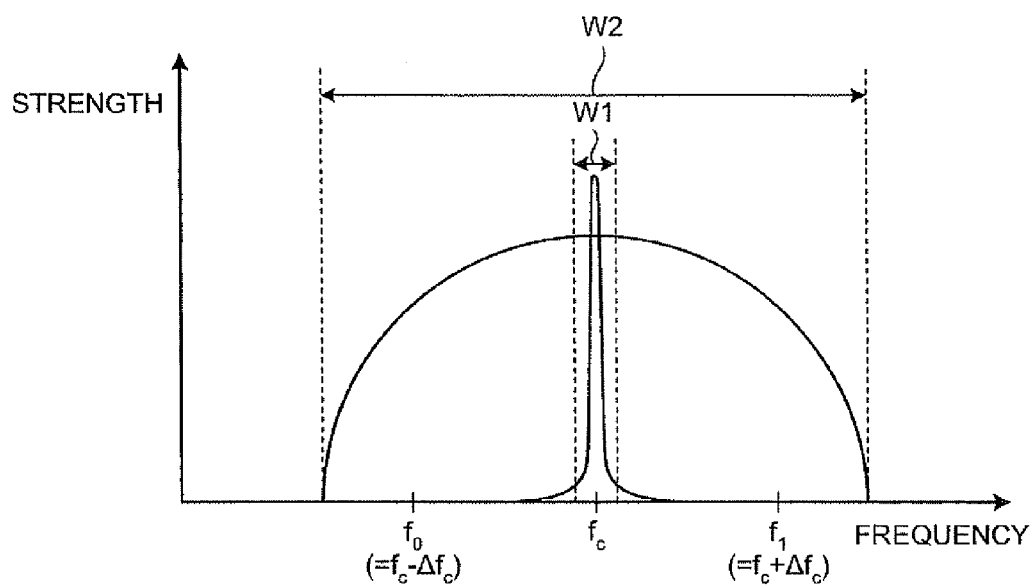
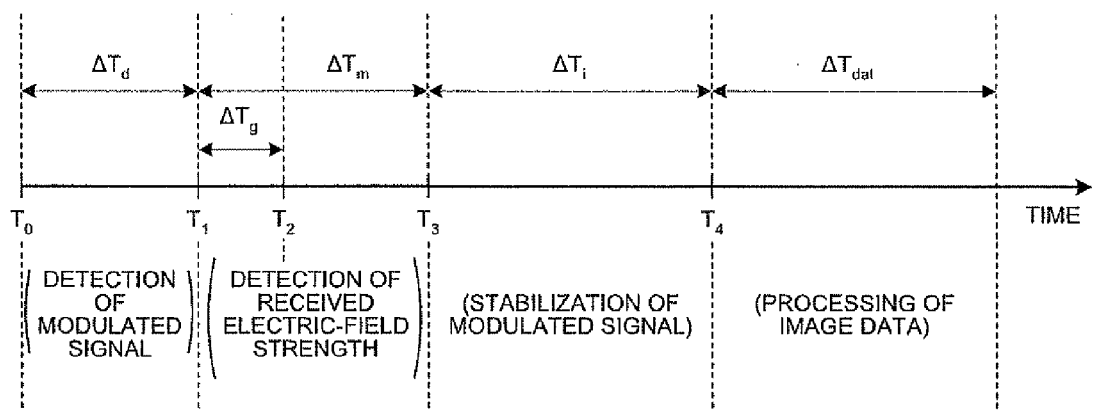

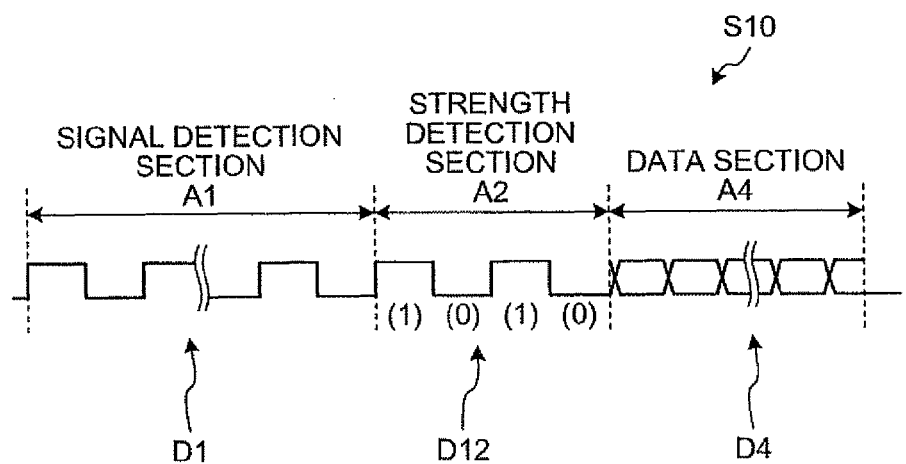
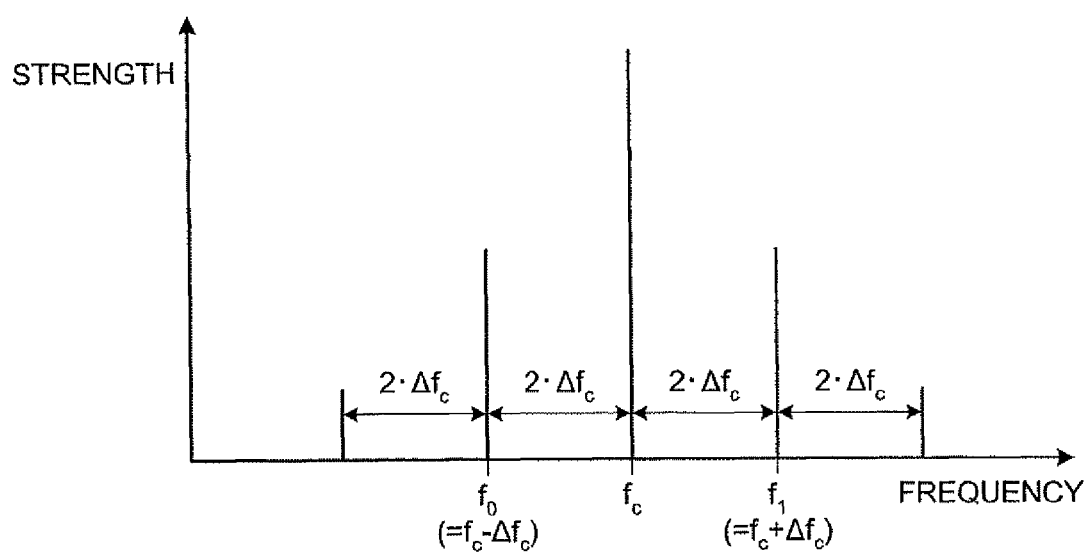

TRANSMITTING/RECEIVING SYSTEM AND MEDICAL SYSTEM

CROSS-REFERENCE TO RELATED APPLICATIONS

This application is based upon and claims the benefit of priority from Japanese Patent Application No. 2007-332936, filed Dec. 25, 2007, the entire contents of which are incorporated herein by reference.

BACKGROUND OF THE INVENTION

1. Field of the Invention

The present invention relates to a transmitting/receiving system in which various types of data are exchanged by wireless communication between a transmitting apparatus and a receiving device, and, more particularly, to a transmitting/receiving system and a medical system in which various types of data including image data are exchanged by broadband wireless communication and a received electric-field strength at which data is received is detected.

2. Description of the Related Art

In the field of endoscopes, capsule endoscopes with an image capturing function and a wireless communication function have been used, and a transmitting/receiving system including a capsule endoscope that wirelessly transmits data about captured images (an example of a transmitting apparatus) and a receiving device provided outside a subject, such as a patient, has been proposed. In the transmitting/receiving system, the capsule endoscope is introduced into the subject from the mouth for observation (examination). Thereafter, until being naturally excreted from the subject, the capsule endoscope sequentially captures images of the internal of the organs (hereinafter, sometimes referred to as "in-vivo images") at predetermined intervals of, for example, 0.5 second while moving through the alimentary canal. Each time when the capsule endoscope captures in-vivo images in the subject, the capsule endoscope wirelessly and sequentially transmits data about the in-vivo images (hereinafter, "in-vivo image data") to the outside.

The in-vivo image data wirelessly transmitted by the capsule endoscope inside the subject is sequentially received by the receiving device. The receiving device receives a wireless signal from the capsule endoscope via a plurality of receiving antennas arranged on the body surface of the subject, and performs predetermined processing including decoding on the wireless signal. In this manner, the receiving device obtains the in-vivo image data about the subject. The in-vivo image data received by the receiving device is sequentially stored in a recording medium inserted into the receiving device. Thereafter, the recording medium is detached from the receiving device and inserted into an image display device. The image display device reads the image data from the receiving device, stores the in-vivo image data in its memory, and displays the in-vivo images on its display based on the in-vivo image data. A user, such as a doctor or a nurse, observes the in-vivo images displayed on the image display device and diagnoses the subject.

As such a system configured to wirelessly exchange various types of data including image data, there is a conventional system in which a signal received via an antenna is branched to a signal strength detecting system and a signal processing system, the signal strength detecting system detects a signal strength of the signal, and the signal processing system performs predetermined signal processing on the signal (for example, see Japanese Patent Application Laid-open No. 2007-049730 or No. 2004-310420).

SUMMARY OF THE INVENTION

A transmitting/receiving system according to an aspect of the present invention includes a transmitting apparatus that generates a modulated signal containing a broadband signal component and a narrowband signal component, and transmits the modulated signal to the outside; and a receiving device that receives the modulated signal via at least three receiving antennas. The receiving device includes a signal processing system that processes the broadband signal component contained in the modulated signal; and a received-strength detecting system that processes the narrowband signal component contained in the modulated signal.

A medical system according to another aspect of the present invention includes a wireless transmitting medical apparatus including a transmitting unit that generates a modulated signal containing a broadband signal component and a narrowband signal component, and that transmits the modulated signal to the outside the wireless medical apparatus; and a receiving device that receives the modulated signal via at least three receiving antennas. The receiving device includes a signal processing system that processes the broadband signal component contained in the modulated signal; and a received-strength detecting system that processes the narrowband signal component contained in the modulated signal. Data about the narrowband signal component processed by the received-strength detecting system is used to detect a position of the wireless transmitting medical apparatus.

The above and other objects, features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 6 is a section diagram of the configuration of the receiving device according to the first embodiment;

FIG. 7 is a schematic diagram of filter characteristics of a narrowband filter and a broadband filter of the receiving device according to the first embodiment;

FIG. 8 is a section diagram of operation timing of the receiving device according to the first embodiment;

FIG. 13 is a schematic diagram of a signal format of a transmission signal from the capsule endoscope according to the fourth embodiment;

FIG. 14 is a schematic diagram of frequency characteristics of a plurality of narrowband signal components contained in an strength detection section of a modulated signal from the capsule endoscope according to the fourth embodiment;

DETAILED DESCRIPTION OF THE PREFERRED EMBODIMENTS

Exemplary embodiments of the present invention are explained in detail below with reference to the accompanying drawings.

Figure 1:
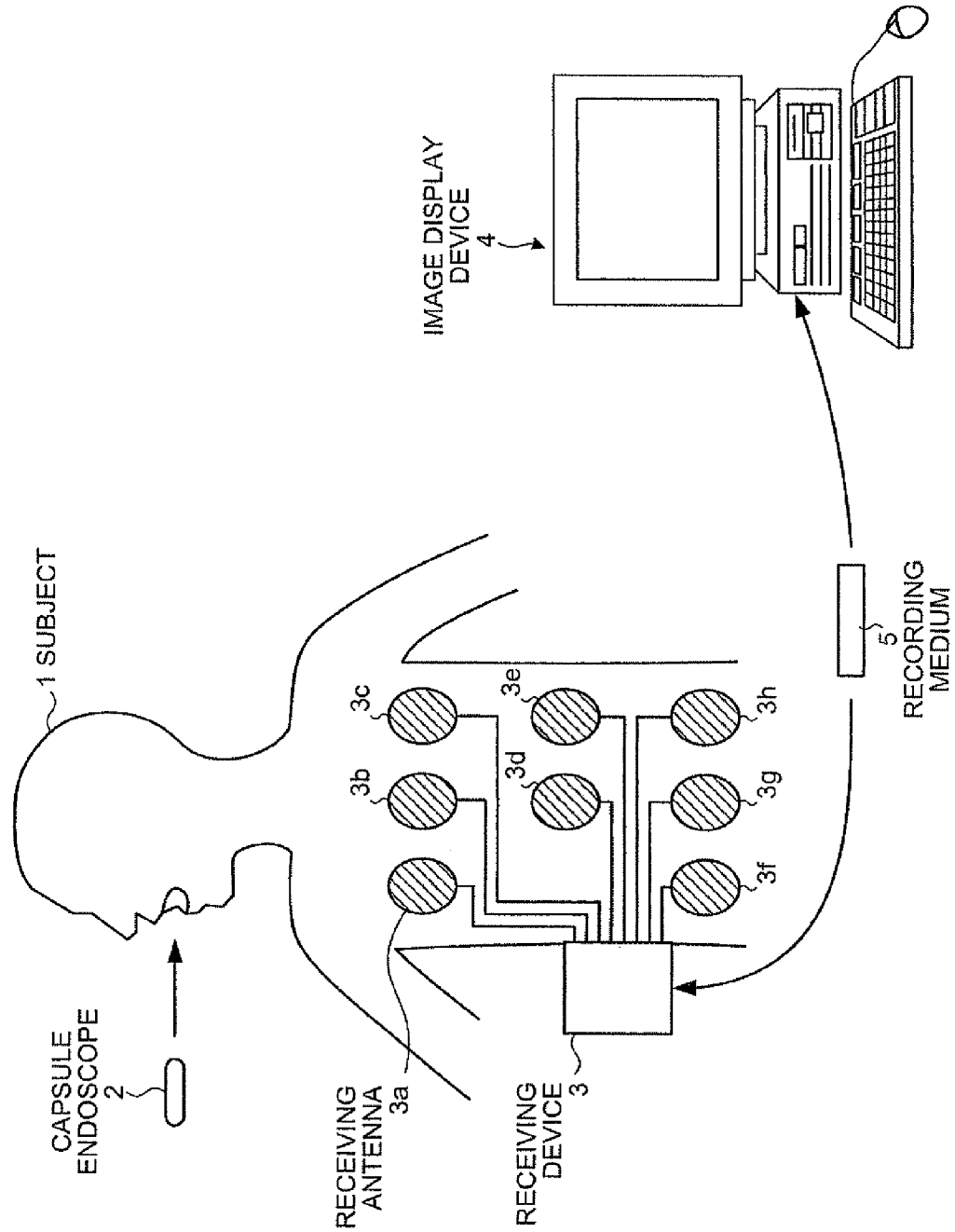
FIG. 1 is a schematic diagram of a configuration of a transmitting/receiving system according to a first embodiment of the present invention.

A transmitting/receiving system according to a first embodiment of the present invention is explained below. FIG. 1 is a schematic diagram of a configuration of the transmitting/receiving system according to the first embodiment. The transmitting/receiving system serves as a medical system that transmits or receives in-vivo data about a subject 1. As shown in FIG. 1, the transmitting/receiving system includes a capsule endoscope 2 that is to be introduced into organs of the subject 1; a receiving device 3 that receives in-vivo data about in-vivo images of the subject 1 wirelessly transmitted from the capsule endoscope 2; an image display device 4 that displays the in-vivo images based on the in-vivo image data received by the receiving device 3; and a recording medium 5 used for exchanging data between the receiving device 3 and the image display device 4.

The capsule endoscope 2 has an image capturing function of capturing an in-vivo image and a wireless communication function for wirelessly transmitting in-vivo image data about the captured image to the outside. Specifically, the capsule endoscope 2 is introduced into the subject 1 from the mouth, and moves through the alimentary canal depending on, for example, peristalsis. The capsule endoscope 2 sequentially captures in-vivo images of the subject 1. Each time when the capsule endoscope 2 captures in-vivo images, the capsule endoscope 2 wirelessly transmits in-vivo image data about the in-vivo images to the outside. Specifically, the capsule endoscope 2 generates a wireless transmission signal containing the in-vivo image data, performs digital modulation on the transmission signal, and wirelessly transmits the transmission signal having undergone digital modulation (hereinafter, "modulated signal") to the receiving device 3 outside the subject 1. Until being naturally excreted from the subject 1 to the outside, the capsule endoscope 2 repeats capturing in-vivo images and wirelessly transmitting in-vivo image data.

The receiving device 3 receives the modulated signal wirelessly transmitted from the capsule endoscope 2. The receiving device 3 includes a received-strength detecting system that detects a received electric-field strength at which the modulated signal is received from the capsule endoscope 2 on a per receiving-antenna basis; and a signal processing system that performs signal processing on the in-vivo image data contained in the modulated signal received from the capsule endoscope 2. The receiving device 3 includes a plurality of receiving antennas 3a to 3h, and receives modulated signals from the capsule endoscope 2 via the receiving antennas 3a to 3h. The receiving device 3 branches the modulated signal as modulated signals to the received-strength detecting system and the signal processing system. The received-strength detecting system detects a received electric-field strength of one of the modulated signals and the signal processing system performs the signal processing on the other modulated signal, so that the in-vivo image of the subject 1 is obtained. The recording medium 5 is detachably inserted into the receiving device 3, and the receiving device 3 stores various types of data including the in-vivo image data in the recording medium 5.

As shown in FIG. 1, the receiving antennas 3a to 3h are arranged separately in predetermined positions on the body surface of the subject 1 (for example, along a route in which the capsule endoscope 2 moves through the interior of the subject 1). The receiving antennas 3a to 3h are connected to the receiving device 3. The receiving antennas 3a to 3h capture modulated signals from the capsule endoscope 2 at the positions shown in FIG. 1, and send the modulated signals to the receiving device 3. It suffices that at least one receiving antenna is arranged on the subject 1. The number of receiving antennas to be arranged on the subject 1 is not limited to 8, and can be arbitrarily changed.

The image display device 4 displays various types of data including the in-vivo images of the subject 1 captured by the capsule endoscope 2. The recording medium is detachably inserted into the image display device 4, and the image display device 4 is configured as, for example, a work station such that the image display device 4 obtains various types of data including the in-vivo image data via the recording medium 5 and displays the various types of data. The image display device 4 can display an image on, for example, a display such as a cathode ray tube (CRT) display or a liquid crystal display (LCD) or output an image on a different medium using, for example, a printer. The data displayed by the image display device 4 includes the position of the capsule endoscope 2 in the subject 1 and patient information, such as the patient name and patient ID, which identifies the subject 1.

The recording medium 5 is portable, and is detachably insertable into the receiving device 3 and the image display device 4. The recording medium 5 is configured to output and store therein data while being inserted into the receiving device 3 or the image display device 4. Specifically, while being inserted into the receiving device 3, the recording medium 5 stores therein various types of data including the in-vivo image data received by the receiving device 3 from the capsule endoscope 2. On the other hand, after the capsule endoscope 2 is excreted from the subject 1, the recording medium 5 is detached from the receiving device 3 and inserted into the image display device 4. While being inserted into the image display device 4, the recording medium 5 outputs the various types of data to the image display device 4. In this manner, the image display device 4 reads the various types of data from the recording medium 5.

Figure 2:
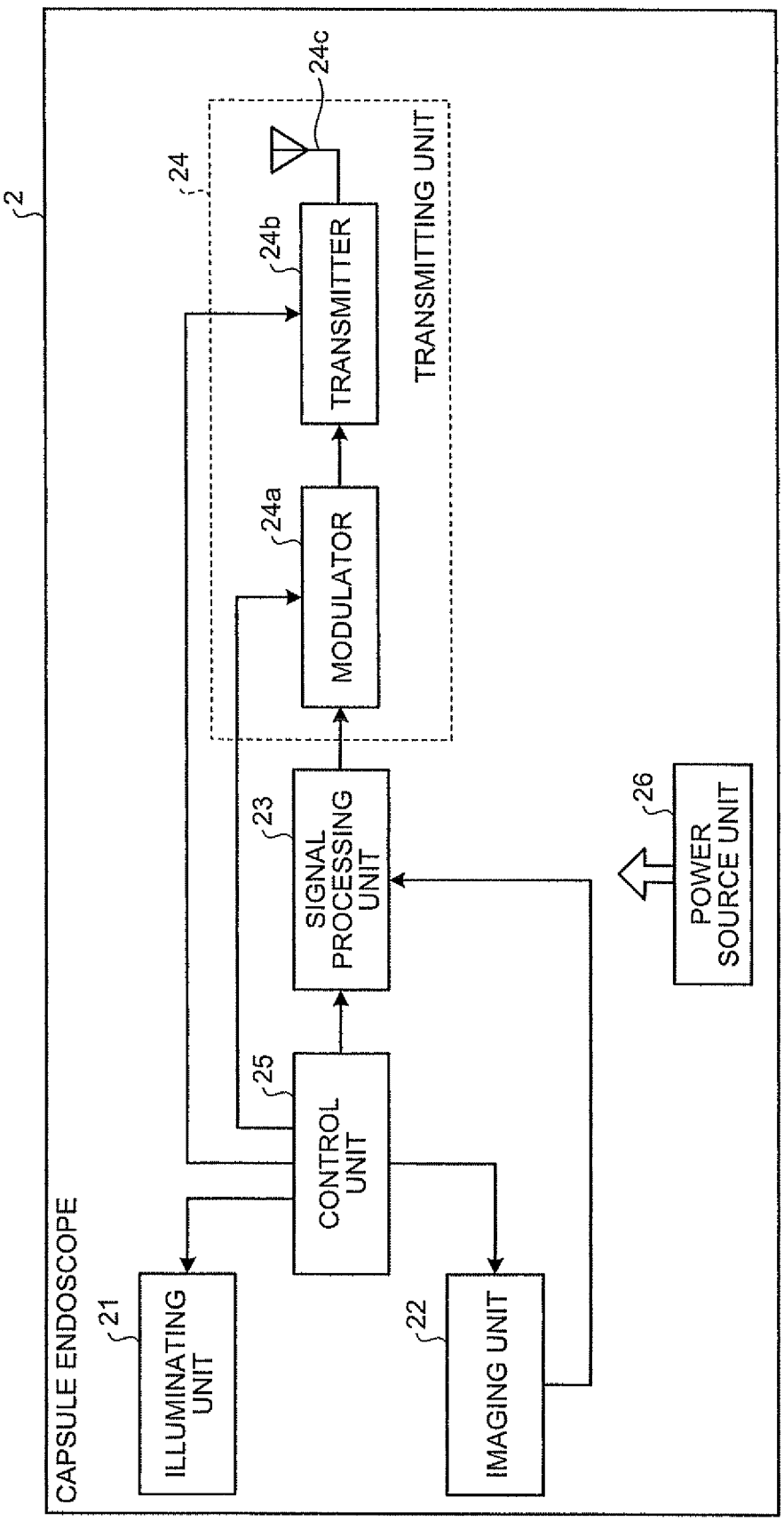
FIG. 2 is a section diagram of a configuration of a capsule endoscope, which serves as a transmitting apparatus, according to the first embodiment.

The configuration of the capsule endoscope 2 is explained in detail below. FIG. 2 is a section diagram of the configuration of the capsule endoscope 2. As shown in FIG. 2, the capsule endoscope 2 includes a illuminating unit 21 that illuminates a target site; an imaging unit 22 that captures an image of the target site illuminated by the illuminating unit 21; a signal processing unit 23 that generates a transmission signal containing in-vivo image data about the in-vivo image captured by the imaging unit 22; a transmitting unit 24 that performs digital modulation on the transmission signal generated by the signal processing unit 23 and wirelessly transmits the modulated transmission signal; a control unit 25 that controls each unit of the capsule endoscope 2; and a power source unit 26 that supplies drive power to each unit of the capsule endoscope 2.

The illuminating unit 21 is a light emitting device such as a light emitting diode (LED). The illuminating unit 21 emits a light under the control by the control unit 25 to illuminate a target site of the interior of the subject 1. The imaging unit 22 includes a solid-state image sensor, such as a charge coupled device (CCD) or a complementary metal oxide semiconductor (CMOS), and an optical system such as a condenser lens. The imaging unit 22 captures an in-vivo image of the interior of the organs of the subject 1, which is illuminated by the illuminating unit 21. The in-vivo image data, which is acquired by the imaging unit 22 and to be exchanged between the capsule endoscope 2 and the receiving device 3, is transmitted to the signal processing unit 23.

The signal processing unit 23 serves as a signal generating unit that generates a transmission signal to be wirelessly transmitted to the receiving device 3 from the capsule endoscope 2. The signal processing unit 23 operates under the control by the control unit 25. Each time when the imaging unit 22 captures an in-vivo image of the subject 1, the signal processing unit 23 receives the in-vivo image data from the imaging unit 22 and generates a transmission signal containing the in-vivo image data. Specifically, the signal processing unit 23 generates a one-frame transmission signal $S_0$ containing one-frame in-vivo image data based on a signal format shown in FIG. 3. The signal processing unit 23 assigns a detection signal containing detection data D1 for signal detection to a signal detection section A1, which is the top signal section of the transmission signal $S_0$, assigns a direct-current (DC) signal containing fixed digital data D2 of a fixed data value to an strength detection section A2 subsequent to the signal detection section A1, assigns an adjustment signal containing digital data D3 for frequency adjustment to an idling section A3 subsequent to the strength detection section A2, and assigns an image signal containing in-vivo image data D4 received from the imaging unit 22 to a data section A4 subsequent to the idling section A3, so that the one-frame transmission signal $S_0$ is generated. The signal processing unit 23 transmits the one-frame transmission signal $S_0$ to the transmission unit 24.

The detection data D1 in the signal detection section A1 is digital data consisting of high-level digital values (1) and low-level digital values (0). The detection data D1 is used by the receiving device 3 to detect the start of the transmission signal $S_0$ (specifically, the start of the modulated signal obtained by performing the digital modulation on the transmission signal $S_0$). The DC signal in the strength detection section A2 is an example of a specific signal with a fixed frequency of 0 Hz, and consists of the fixed digital data D2. The adjustment signal in the idling section A3 consists of the digital data D3 in which the digital value (1) and the digital value (2) are alternately repeated. The DC signal is used to correct deviation of the frequency, which is caused when data shifts from the fixed digital data D2 in the strength detection section A2 to the in-vivo image data D4 in the data section A4.

Figure 3:
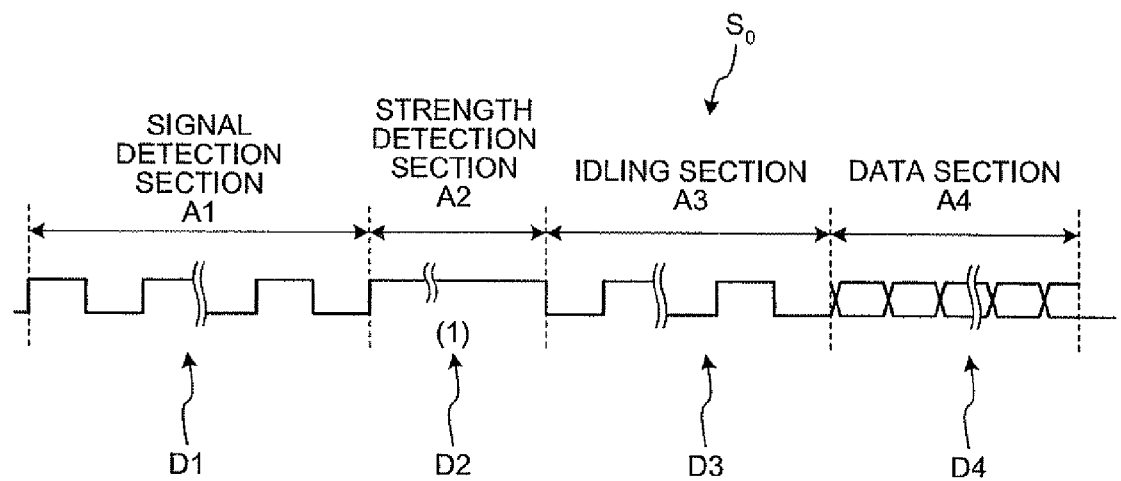
FIG. 3 is a schematic diagram of a signal format of a transmission signal from a capsule endoscope according to the first embodiment.

The DC signal in the strength detection section A2 can consist of the fixed digital data of the fixed digital value (1) as shown in FIG. 3 or the fixed digital Data D2 of the fixed digital value (1).

The transmitting unit 24 performs the digital modulation on the transmission signal $S_0$ generated by the signal processing unit 23 and wirelessly transmits the modulated signal to the outside. Specifically, the transmitting unit 24 includes a modulator 24a that performs frequency shift keying (FSK) on the transmission signal $S_0$ generated by the signal processing unit 23; and a transmitter 24b that wirelessly transmits the transmission signal $S_0$ modulated by the modulator 24a. In the first embodiment, the transmitting unit 24 transmits the modulated signal obtained by the FSK. Alternatively, the transmitting unit 24 can be configured to perform other types of modulation other than the FSK.

The modulator 24a performs the FSK on the transmission signal $S_0$ generated by the signal processing unit 23, thereby generating a modulated signal containing, in the strength detection section A2, a narrowband signal component corresponding to the DC signal containing the fixed digital data D2. Specifically, the modulator 24a includes a signal sending unit that sends a signal (carrier signal) of a carrier frequency $f_c$ and a voltage controlled oscillator (VCO). Under the control by the control unit 25, the modulator 24a receives the transmission signal $S_0$ from the signal processing unit 23. Each time when the modulator 24a receives a transmission signal $S_0$ from the signal processing unit 23, the modulator 24a performs the FSK by overlaying the transmission signal $S_0$ and the carrier signal. The modulator 24a generates a modulated signal by performing the FSK on the transmission signal $S_0$, while performing phase locked loop (PLL) control for fixing the frequency to the carrier frequency. The modulator 24a sends the modulated signal to the transmitter 24b.

Figure 4:
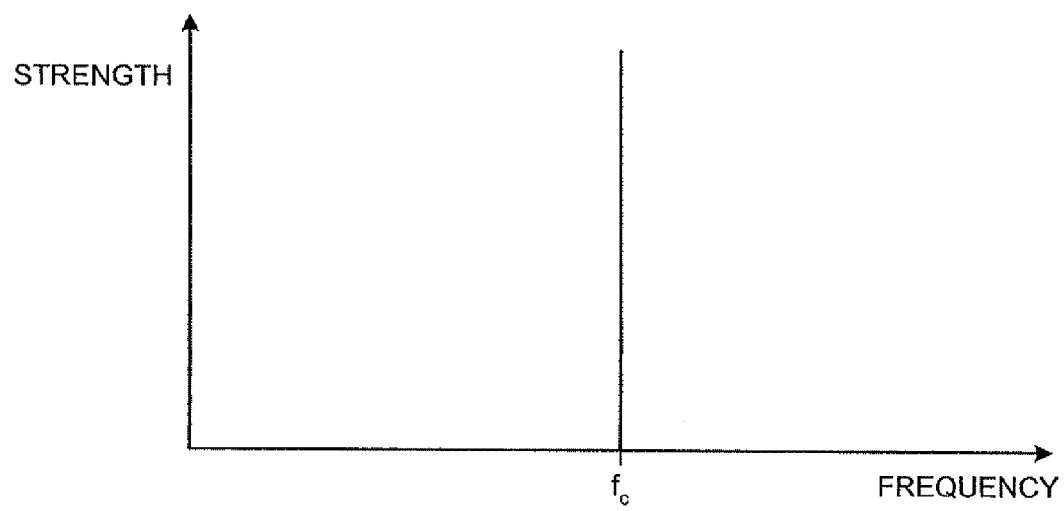
FIG. 4 is a schematic diagram of frequency characteristics of a narrowband signal component contained in an strength detection section of a modulated signal from the capsule endoscope according to the first embodiment.

The modulated signal generated by performing the FSK by the modulator 24a contains a broadband signal component corresponding to the detection data D1 in the signal detection section A1, contains the narrowband signal component corresponding to the DC signal containing the fixed digital data D2 in the strength detection section A2, contains a broadband signal component corresponding to the digital data D3 in the idling section A3, and contains a broadband signal component corresponding to the in-vivo image data D4 in the data section A4. When the signal of the strength detection section A2 is a DC signal consisting of the fixed digital data D2, the PLL control is performed by the modulator 24a, so that the frequency of the DC signal is attenuated to the carrier frequency. As a result, the modulator 24a generates the modulated signal containing the carrier signal (i.e., single-frequency unmodulated signal), which is the narrowband signal component, in the strength detection section A2. As shown in FIG. 4, the frequency characteristics of the modulated signal in the strength detection section A2 are those of the narrowband signal component having a frequency spectrum at the carrier frequency $f_c$. A bandwidth of the carrier signal, which is the narrowband signal component, is, for example, about several tens of kHz.

Figure 5:
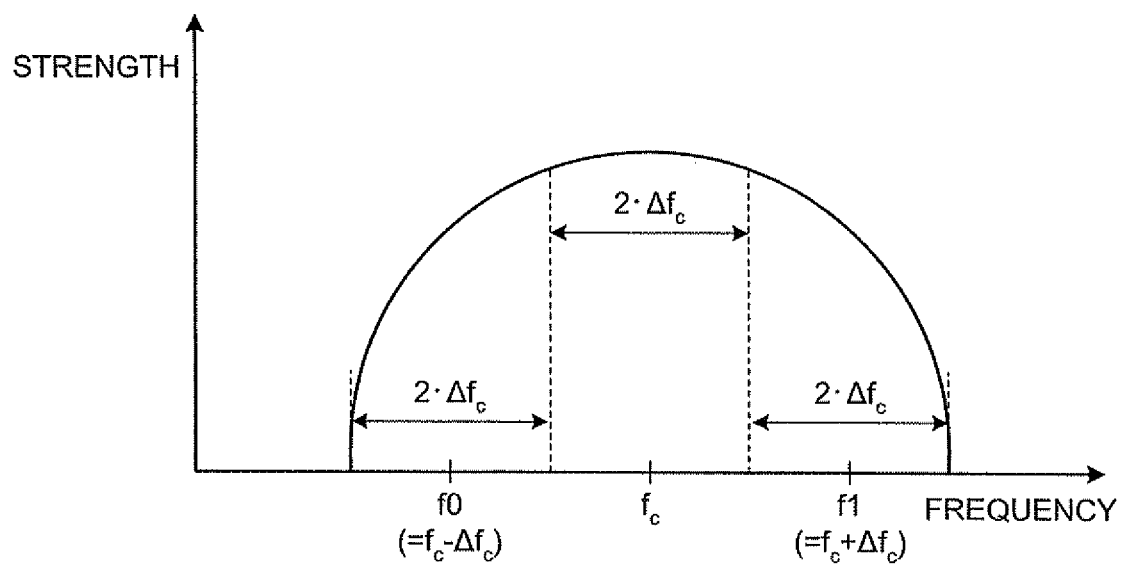
FIG. 5 is a schematic diagram of frequency characteristics of a broadband signal component contained in the modulated signal from the capsule endoscope according to the first embodiment.

On the other hand, as shown in FIG. 5, the broadband signal components contained in the respective signal detection section A1, the idling section A3, and the data section A4 of the modulated signal have the frequency characteristics of an occupied bandwidth obtained by adding together a bandwidth twice a frequency deviation $\Delta f_c$ (one side) from the carrier frequency fc, a band width twice a frequency deviation $\Delta f_c$ from a frequency $f_0$ ($=f_c-\Delta f_c$) corresponding to a digital value (0), and a band width twice a frequency deviation $\Delta f_c$ from a frequency $f_1$ ($=f_c-\Delta f_c$) corresponding to a digital value (1).

The occupied broadband signal component is, for example, not smaller than several MHz.

The transmitter 24b wirelessly transmits the modulated signal generated by the modulator 24a to the outside. The transmitter 24b receives the modulated signal from the modulator 24a under the control by the control unit 25. Each time when the transmitter 24b receives a modulated signal, the transmitter 24b increases the frequency of the modulated signal and wirelessly transmits the high-frequency modulated signal. The transmitter 24b includes a transmitting antenna 24c, and wirelessly transmits the high-frequency modulated signal to the receiving device 3 shown in FIG. 3 via the transmitting antenna 24c.

The control unit 25 includes a CPU that executes a processing program, a ROM that previously stores therein the processing program, and a RAM that stores therein operation parameters of each processing, etc. The control unit 25 controls each unit of the capsule endoscope 2. Specifically, the control unit 25 controls the operations of the illuminating unit 21, the imaging unit 22, the signal processing unit 23, the modulator 24a, and the transmitter 24b, and controls input and output of signals between the imaging unit 22, the signal processing unit 23, the modulator 24a, and the transmitter 24b.

The power source unit 26 includes a battery having a predetermined power and a switching unit that switches between on and off states. In the on state, the power source unit 26 supplies power to each unit (the illuminating unit 21, the imaging unit 22, the signal processing unit 23, the modulator 24a, the transmitter 24b, and the control unit 25) of the capsule endoscope 2. In the off state, the power source unit 26 stops supplying drive power to each unit of the capsule endoscope 2.

The configuration of the receiving device 3 is explained in detail below. FIG. 6 is a section diagram of the receiving device 3. As shown in FIG. 6, the receiving device 3 includes the receiving antennas 3a to 3h; an antenna switching unit 30 that selectively switches between the receiving antennas 3a to 3h; a radio frequency (RF) filter 31; and a low noise amplifier (LNA) 32. The receiving device 3 further includes a frequency mixer 33 that branches the signal received from the capsule endoscope 2; a received-strength detecting system 40 that detects a received electric-field strength on a per receiving-antenna basis; and an image processing system 41 that performs signal processing on the in-vivo image data contained in the received signal. The receiving device 3 further includes an input unit 42, a display unit 43, a storing unit 44, a control unit 45, and a power source unit 46.

The antenna switching unit 30 is used to arbitrarily select, from the receiving antennas 3a to 3h shown in FIG. 1, a receiving antenna via which the modulated signal wirelessly transmitted from the capsule endoscope 2 is to be received. The antenna switching unit 30 is connected to the receiving antennas 3a to 3h via cables, selects one of the receiving antennas 3a to 3h under the control by the control unit 45, and connects the selected receiving antenna to the RF filter 31. Under the control by the control unit 45, the antenna switching unit 30 sequentially switches between the receiving antennas 3a to 3h, i.e., selects a receiving antenna to be electrically connected to the RF filter 31. The modulated signal received from the capsule endoscope 2 by the antenna switching unit 30 via a selected one of the receiving antennas 3a to 3h is sent to the RF filter 31.

The RF filter 31 is a bandpass filter having a pass bandwidth (for example, a bandwidth not smaller than several MHz) with which the broadband signal component contained in the modulated signal from the capsule endoscope 2 can be passed. The RE filter 31 receives the modulated signal, which is transmitted from the capsule endoscope 2, from the antenna switching unit 30, and passes the signal within the pass bandwidth, i.e., the modulated signal from the capsule endoscope 2. The modulated signal having passed thorough the RF filter 31 is sent to the LNA 32. The LNA 32 receives the modulated signal, which is transmitted from the capsule endoscope, from the RF filter 31, and amplifies the modulated signal having passed through the RF filter 31. The modulated signal amplified by the LNA 32 is sent to the frequency mixer 33.

The frequency mixer 33 has a frequency converting function for converting (downconverting) the frequency of the modulated signal to an intermediate frequency by mixing the modulated signal from the capsule endoscope 2 with a signal of a different frequency, and a signal branching function for branching the modulated signal of the intermediate frequency to the received-strength detecting system 40 and the image processing system 41. Specifically, the frequency mixer 33 receives the modulated signal from the capsule endoscope 2, which is amplified by the LNA 32, and downconverts the high-frequency to the intermediate frequency of the modulated signal by mixing the modulated signal with the signal of the different frequency. The frequency mixer branches the downconverted modulated signal (i.e., the modulated signal of the intermediate frequency) as modulated signals and outputs the modulated signals to the received-strength detecting system 40 and the image processing system 41. A modulated signal $S_1$, which is one of the modulated signals branched by the frequency mixer 33, is sent to the received-strength detecting system 40, and a modulated signal $S_2$, which is the other modulated signal, is sent to the image processing system 41.

The received-strength detecting system 40 detects field intensities, i.e., the received electric-field strengths, of modulated signals received from the capsule endoscope 2 via the receiving antennas 3a to 3h on a per receiving-antenna basis. The received-strength detecting system 40 includes a narrowband filter 34, an intermediate frequency amplifier 35, and a received-strength detecting unit 36.

The narrowband filter 34 is a bandpass filter that extracts the narrowband signal component contained in the modulated signal received from the capsule endoscope 2 received via one of the receiving antennas 3a to 3h. Specifically, as shown in FIG. 7, the narrowband filter 34 has a pass bandwidth $W_1$ wider than that of the narrowband signal component (i.e., carrier signal) in the strength detection section A2 and narrower than the occupied bandwidth of the modulated signal $S_1$ (i.e., the broadband signal component contained in the modulated signal $S_1$). The narrowband filter 34 receives the modulated signal $S_1$ branched by the frequency mixer 33, and extracts the narrowband signal component of the modulated signal $S_1$. The narrowband signal component of the modulated signal $S_1$ extracted by the narrowband filter 34 is sent to the intermediate frequency amplifier 35. The intermediate frequency amplifier 35 amplifies the narrowband signal component of the modulated signal $S_1$, which is extracted by the narrowband filter 34, and sends the amplified narrowband signal component of the modulated signal $S_1$ to the received-strength detecting unit 36. The pass bandwidth $W_1$ of the narrowband filter 34 is not smaller than one-ten-thousandth of a pass bandwidth $W_2$ (for example, between few MHz to 10 MHz) of a broadband filter 37 and not larger than one-tenth of the pass bandwidth $W_2$. Specifically, the pass bandwidth $W_1$ is about several kHz to 100 kHz.

The received-strength detecting unit 36 detects received electric-field strengths of modulated signals received from the capsule endoscope 2 via the receiving antennas 3a to 3h on a per receiving-antenna basis. Specifically, the received-strength detecting unit 36 receives the narrowband signal component of the modulated signal $S_1$ amplified by the intermediate frequency amplifier 35, and detects the received electric-field strength of the narrowband signal component, i.e., the carrier signal contained in the strength detection section A2 of the modulated signal $S_1$. The received-strength detecting unit 36 converts an analog signal, such as a received signal strength indicator (RSSI), indicating the detected received electric-field strength into a digital RSSI signal, and sends the digital RSSI signal as the result of the received electric-field strength detection to the control unit 45. Each time when the antenna switching unit 30 switches between the receiving antennas $3a$ to $3h$, i.e., selects the receiving antenna via which a modulated signal is to be received from the capsule endoscope 2, the received-strength detecting unit 36 detects a received electric-field strength of a narrowband signal component (carrier signal) of a modulated signal $S_1$ received from the intermediate frequency amplifier 35, and sends the result of detecting the received electric-field strength to the control unit 45 on a per receiving antenna basis.

The image processing system 41 functions as a signal processing system that performs signal processing on predetermined data, i.e., the image data (specifically, the in-vivo image data of the in-vivo image captured by the capsule endoscope 2), contained in the modulated signal from the capsule endoscope 2 via one of the receiving antennas $3a$ to $3h$. The image processing system 41 includes the broadband filter 37, an intermediate frequency amplifier 38, and an image processing unit 39.

The broadband filter 37 is a bandpass filter that extracts the broadband signal component contained in the modulated signal from the capsule endoscope 2 received via one of the receiving antennas $3a$ to $3h$. Specifically, as shown in FIG. 7, the broadband filter 37 has the pass bandwidth $W_2$ wider than the occupied band width of the modulated signal $S_2$. The broadband filter 37 receives the modulated signal $S_2$ branched by the frequency mixer 33, and extracts the broadband signal component and the narrowband signal component, i.e., signal components within the pass bandwidth $W_2$, contained in the modulated signal $S_2$. The signal components extracted by the broadband filter 37 are, for example, the broadband signal component corresponding to the detection data D1 in the signal detection section A1, the narrowband signal component in the strength detection section A2, the broadband signal component corresponding to the digital data D3 in the idling section A3, and the broadband signal component corresponding to the in-vivo image data D4 in the data section A4. The signal components of the modulated signal $S_2$ extracted by the broadband filter 37 are sent to the intermediate frequency amplifier 38. The intermediate frequency amplifier 38 amplifies the signal components of the modulated signal $S_2$ extracted by the broadband filter 37, and sends the amplified signal components of the modulated signal $S_2$ to the image processing unit 39.

The image processing unit 39 performs the signal processing on the in-vivo image data contained in the modulated signal received from the capsule endoscope 2 via one of the receiving antennas $3a$ to $3h$, and generates the in-vivo image of the subject 1 corresponding to the in-vivo image data. Specifically, the image processing unit 39 receives the modulated signal $S_2$ amplified by the intermediate frequency amplifier 38, and demodulates the modulated signal $S_2$ to an image signal by performing predetermined demodulation processing on the modulated signal $S_2$. The image processing unit 39 extracts the in-vivo image data D4 contained in the image signal, performs the signal processing on the in-vivo image data D4, thereby generating the in-vivo image of the subject 1. Each time when the antenna switching unit 30 switches between the receiving antennas $3a$ to $3h$, i.e., selects the receiving antenna via which a modulated signal from the capsule endoscope 2 is to be received, the image processing unit 39 demodulates a modulated signal $S_2$ received from the intermediate frequency amplifier 38 to obtain in-vivo image data D4, and generates an in-vivo image corresponding to the in-vivo image data D4. In-vivo images generated by the image processing unit 39 are sequentially sent to the control unit 45.

The input unit 42 is an input key. The input unit 42 inputs various types of information including instruction information for giving an instruction to the control unit 45. The information to be input to the control unit 45 by the input unit 42 includes instruction information about an instruction for starting receiving a modulated signal from the capsule endoscope 2, instruction information about an instruction for display (output), the patient information including the patient name, patient ID, examination date (date at which the capsule endoscope 2 is introduced into the subject 1).

The display unit 43 includes light emitting diodes (LEDs) and a liquid crystal display. Under the control by the control unit 45, the display unit 43 displays various types of information such as the operation status of the receiving device 3 (indicating that the receiving device 3 is receiving information or is in the wait state), an in-vivo image of the subject 1, the patient information about the subject 1, and the examination date.

The recording medium 5 shown in FIG. 1 is detachably inserted into the storing unit 44. The storing unit 44 stores, in the recording medium 5, various types of data under the control by the control unit 45. The data to be stored (saved) in the recording medium 5 by the storing unit 44 includes the in-vivo image of the subject 1, the data about the position of the capsule endoscope 2 in the subject 1.

The storing unit 44 can be configured to include a memory integrated circuit (IC), such as a random access memory (RAM) or a flash memory, or a hard disk such that the storing unit 44 stores therein various types of data including the in-vivo image of the subject 1. In this case, the receiving device 3 can transmit the various types of data from the storing unit 44 to the image display device 4 shown in FIG. 1 by wired communication or wireless communication.

The control unit 45 includes a CPU that executes a processing program, a ROM that previously stores therein the processing program, and a RAM that stores therein operation parameters in each processing or the information input by the input unit 42. The control unit 45 controls each unit of the receiving device 3, and controls input and output of signals between the units. Specifically, the control unit 45 controls the antenna switching unit 30 based on the instruction information input by the input unit 42 to control the start and end of receiving modulated signals from the capsule endoscope 2. The control unit 45 causes the display unit 43 to display the in-vivo image of the subject 1 or the patient information based on the instruction information input by the input unit 42. The control unit 45 can cause the display unit 43 to display the in-vivo image read from the storing unit 44. Meanwhile, the control unit 45 causes the antenna switching unit 30 to sequentially switching between the receiving antennas $3a$ to $3h$, i.e., the receiving antenna via which a modulated signal is to be received (caught) from the capsule endoscope 2, and controls the timing at which the received-strength detecting unit 36 and the image processing unit 39 starts the operation. Specifically, the control unit 45 causes the received-strength detecting unit 36 and the image processing unit 39 to perform respectively the processing on the broadband signal component in the image processing system 41 and the processing on the narrowband signal component in the received-strength detecting system 40 based on the time sharing system. The control unit 45 can synchronizes the timing at which the antenna switching unit 30 is caused to switch between the receiving antennas and the timing at which the received-strength detecting unit 36 and the image processing unit 39 starts the operation.

The control unit 45 includes a position calculator 45a that calculates the position of the capsule endoscope 2 in the subject 1. The position calculator 45a receives the received electric-field strength of one of the receiving antennas 3a to 3h, and calculates the data about the position of the capsule endoscope 2 in the subject 1 based on the received electric-field strength. Specifically, the position calculator 45a has predetermined position coordinate data about each of the receiving antennas 3a to 3h, and selects the top three received electric-field strengths from the received electric-field intensities of the receiving antennas 3a to 3h received on a per one-frame modulated signal basis. The position calculator 45a calculates data about the position of the capsule endoscope 2 in the subject 1 based on, for example, the three-point cross method using the top three received electric-field strengths and the position coordinate data about the three receiving antennas corresponding to the top three received electric-field strengths among the receiving antennas 3a to 3h.

The data about the position of the capsule endoscope 2, which is calculated by the position calculator 45a, is stored, in the storing unit 44 (specifically, in the recording medium 5), in association with the in-vivo image generated by the image processing unit 39. Specifically, the control unit 45 associates the in-vivo image of the subject 1 based on the in-vivo image data D4 in the modulated signal $S_2$ corresponding to any one of the top three reception eclectic field intensities (the highest received electric-field strength is desirable) with the data about the position of the capsule endoscope 2, and stores, in the recording medium 5, the in-vivo image and the data about the position of the capsule endoscope 2 associated with each other.

The power source unit 46 includes a battery having predetermined power and a switching unit that switches between the on state and the off state. In the on state, the power source unit 46 supplies necessary drive power to each unit of the receiving device 3. In the off state, the power source unit 46 stops supplying drive power to each unit of the receiving device 3.

The operations of the received-strength detecting unit 36 and the image processing unit 39 of the receiving device 3 are explained below. FIG. 8 is a schematic diagram of operation timing of the receiving device 3. Explained below with reference to FIG. 8 is the operation of the receiving device 3 for detecting a received electric-field strength of a one-frame modulated signal obtained by performing the digital modulation on the one-frame transmission signal $S_0$ and for performing the signal processing on the in-vivo image data.

The receiving device 3 receives the modulated signal from the capsule endoscope 2 via the receiving antenna selected from the receiving antennas 3a to 3h by the antenna switching unit 30, and the frequency mixer 33 branches the modulated signal as the modulated signals $S_1$ and $S_2$. The control unit 45 causes the received-strength detecting unit 36 and the image processing unit 39 to start the operation at the timing (time $T_0$) at which the control unit 45 causes the antenna switching unit 30 to select the receiving antenna.

The image processing unit 39 starts the operation under the control by the control unit 45, and detects that the one-frame modulated signal is wirelessly transmitted from the capsule endoscope 2 from the time $T_0$ until a signal detection period $\Delta T_d$ passes. The image processing unit 39 receives the broadband signal component in the signal detection section A1 of the modulated signal $S_2$ having passed through the broadband filter 37, and detects the start of the modulated signal $S_2$ based on the detection data D1 contained in the broadband signal component.

The signal detection period $\Delta T_d$ is previously set in the image processing unit 39 for determining the start of the one-frame modulated signal. The signal detection period $\Delta T_d$ is long enough for the image processing unit 39 to detect the start of the modulated signal based on the detection data D1.

The received-strength detecting unit 36 detects the received electric-field strength of the modulated signal $S_1$, i.e., the received electric-field strength of each receiving antenna, from the timing (time $T_1$) at which the signal detection period $\Delta T_d$ passes until a strength detection period $\Delta T_m$ passes. Specifically, the received-strength detecting unit 36 waits to start the processing for detecting the received electric-field strength from the time $T_1$ until a guard period $\Delta T_g$ passes, and starts the processing for detecting the received electric-field strength at the timing (time $T_2$) at which the guard period $\Delta T_g$ passes. In the strength detection period $T_m$, the received-strength detecting unit 36 extracts the narrowband signal component, i.e., the carrier signal, contained in the strength detection section A2 of the modulated signal $S_1$ and detects the received electric-field strength of the carrier signal. The received electric-field strength of the carrier signal, which is detected by the received-strength detecting unit 36, is sent to the control unit 45 as the result of the received electric-field strength detection on a per receiving-antenna basis.

The guard period $\Delta T_g$ is previously set in the received-strength detecting unit 36 for stabilizing the frequency of the narrowband signal component in the strength detection section A2 to a predetermined frequency (specifically, the carrier frequency). The guard period $\Delta T_g$ is long enough to cancel the state in which the instability of the frequency is caused when the signal component of the one-frame modulated signal shifts from that in the signal detection section A1 to that in the strength detection section A2. Because the received-strength detecting unit 36 waits to start the processing for detecting the received electric-field strength for the guard period $\Delta T_g$ in the strength detection period $\Delta T_m$, the frequency of the narrowband signal component in the strength detection section A2 to the carrier frequency $f_c$, so that the narrowband signal component with a stable signal level with few variations (i.e., approximately fixed level) can be obtained. Because the received-strength detecting unit 36 detects the received electric-field strength of the narrowband signal component at the stable signal level, the received-strength detecting unit 36 can detect a received electric-field strength of each receiving antenna with high accuracy.

The strength detection period $\Delta T_m$ is long enough for the received-strength detecting unit 36 to detect the received electric-field strength of the one-frame modulated signal, and is previously set in the received-strength detecting unit 36 and the image processing unit 39. It is desirable that the strength detection period $\Delta T_m$ be not shorter than a total value of the signal detection period $\Delta T_d$, the guard period $\Delta T_g$, and a strength measurement period $T_{means}$ (i.e., a processing time necessary for the received-strength detecting unit 36 to detect the received electric-field strength). This is because, if the strength detection period $\Delta T_m$ is set as described, the received-strength detecting unit 36 can assuredly detect the received electric-field strength of the narrowband signal component contained in the strength detection section A2 of the modulated signal $S_2$ after the guard period $\Delta T_g$ passes in the strength detection period $\Delta T_m$.

On the other hand, the image processing unit 39 receives the modulated signal $S_2$ and waits to start the signal processing on the in-vivo image data from the timing (time $T_1$) at which the signal detection period $\Delta Td$ passes until the strength detection period $\Delta T_m$ passes and from the timing (time $T_3$) at which the strength detection period $\Delta T_m$ passes until an idling period $\Delta T_i$ passes. The signal component of the modulated signal $S_2$ to be input to the image processing unit 39 shifts from the narrowband signal component in the strength detection section A2 to the broadband signal component in the idling section A3.

The idling period $\Delta T_i$ is long enough to correct (cancel) the deviation of the frequency caused when the signal component shifts from the narrowband signal component in the strength detection section A2 to the broadband signal component in the data section A4 in the one-frame modulated signal. The idling period $\Delta T_i$ is previously set in the received-strength detecting unit 36 and the image processing unit 39. The image processing unit 39 waits to start the signal processing from the timing at which the narrowband signal component in the strength detection section A2 of the modulated signal $S_2$ is obtained, i.e., from the time $T_3$ shown in FIG. 8, for the idling period $\Delta T_i$, so that the center frequency of the broadband signal component of the modulated signal $S_2$ is attenuated to the carrier frequency and the frequency deviation $\Delta f_c$ is stabilized. After the idling period $\Delta T_i$, the broadband signal component of the modulated signal $S_2$ to be input to the image processing unit 39 enters a state in which the frequency is equally deviated from the carrier frequency $f_c$, i.e., the state preferable to the broadband signal component of the modulated signal $S_2$. It is desirable that the broadband signal component of the modulated signal $S_2$ be longer than the guard period $\Delta T_g$. If the modulated signal $S_2$ is longer than the guard period $\Delta T_g$, the broadband signal component of the modulated signal $S_2$ enters the preferable state in the idling period $\Delta T_i$.

The image processing unit 39 performs the signal processing on the in-vivo image data D4 contained in the data section A4 of the modulated signal $S_2$ from the timing (time $T_4$) at which the idling period $\Delta T_i$ passes until a data processing period $\Delta_{dat}$ passes. In other words, in the data processing period $\Delta T_{dat}$, the image processing unit 39 receives the one-frame in-vivo image data D4 and generates the one-frame in-vivo image based on the in-vivo image data D4. The image processing unit 39 sends the one-frame in-vivo image, i.e., the in-vivo image of the subject 1, to the control unit 45.

Thereafter, the image processing unit 39 enters a wait state until the control unit 45 gives an instruction for stating the operation to the image processing unit 39. In the idling period $\Delta T_i$ and the data processing period $\Delta T_{dat}$, the received-strength detecting unit 36 receives the modulated signal $S_1$, waits to start the processing for detecting the received electric-field strength, and continues the wait state until the control unit 45 gives an instruction for starting the operation to the received-strength detecting unit 36. Each time when the control unit 45 gives the instruction for starting the operation, the received-strength detecting unit 36 and the image processing unit 39 repeatedly performs the operations described above according to the operation timing shown in FIG. 8. As a result, the received-strength detecting unit 36 sequentially detects the received electric-field strengths of the receiving antennas and the image processing unit 39 sequentially generates one-frame in-vivo images.

The unmodulated carrier signal, which is the narrowband signal component having an approximately fixed signal level, is contained in the strength detection section A2 of the modulated signal $S_1$ from which the received electric-field strength is to be detected by the received-strength detecting unit 36. Therefore, the pass bandwidth $W_1$ of the narrowband filter 34 that extracts the narrowband signal component in the strength detection section A2 can be set extremely narrower than the pass bandwidth $W_2$ of the broadband filter 37 (i.e., the pass bandwidth of the band pass filter that extracts the broadband signal component containing the in-vivo image data D4). This reduces the noise input to the received-strength detecting unit 36 and increases the SN ratio of the narrowband signal component, so that the lower limit of received electric-field strength detectable by the received-strength detecting unit 36 can be lowered and the dynamic range of received electric-field strength can be increased. In addition, the received-strength detecting unit 36 can stably detect a received electric-field strength at which a modulated signal containing in-vivo image data D4 from the capsule endoscope 2 on a per receiving-antenna basis.

The received electric-field strengths detected by the received-strength detecting unit 36 on a per receiving-antenna basis are useful for a predetermined application for, for example, detecting the position of the capsule endoscope 2. Specifically, as explained above, the position calculator 45a receives the received electric field strengths of the receiving antennas 3a to 3h, and calculates (detects) the data about the position of the capsule endoscope 2 in the subject 1 using a predetermined number (for example, three) of top received electric-field strengths of the received electric-field strengths. The position calculator 45a compares the received electric-field strengths of the receiving antennas 3 at 3h to each other and selects the predetermined number of top receiving antennas based on the result of the comparison.

However, in a conventional technology for detecting a received electric-field strength of a broadband signal component extracted by a broadband filter, the lower limit of detectable reception eclectic field strength increases depending on the pass bandwidth of the broadband filter. This leads to a state in which the reception electric strength is hidden in noise, i.e., in which the values (voltages) of received electric-field strengths of receiving antennas are approximately equal to each other, which makes it difficult to calculate data about the position of the capsule endoscope 2 in the subject 1 with high accuracy.

For example, when the capsule endoscope 2 in the subject 1 is positioned near the receiving antenna 3d out of the receiving antennas 3a to 3h shown in FIG. 1 on the body surface of the subject 1, the received electric-field strength of the receiving antenna 3d is sufficiently larger than those of the receiving antennas 3a to 3c and 3e to 3h. Therefore, the position calculator 45a can select the received electric-field strength of the receiving antenna 3d as a top strength. However, if the received electric-field strengths of the receiving antennas 3a to 3c and 3e to 3h other than 3d are lower than the lower limit of detectable received electric-field strength, they are hidden in noise and are at approximately equal levels. This makes it difficult to accurately compare the received electric-field strengths of the receiving antennas 3a to 3c and 3e to 3h. As a result, it becomes difficult to calculate the data about the position of the capsule endoscope 2 in the subject 1 with high accuracy.

On the other hand, in the transmitting/receiving system according to the first embodiment, the narrowband signal component (carrier signal) with the approximately fixed signal level is assigned to the strength detection section A2 of the modulated signal to be wirelessly exchanged between the capsule endoscope 2 and the receiving device 3, and the received electric-field strength of the narrowband signal component extracted from the strength detection section A2 is detected. Therefore, the pass bandwidth corresponding to the narrowband signal component can be set in the band pass filter (the narrowband filter 34), which lowers the lower limit of received electric-field strength detectable by the received-strength detecting unit 36 and increases the dynamic range of the received electric-field strength. As a result, even if the received electric-field strengths of the receiving antennas 3a to 3h are very small, the position calculator 45a can assuredly detect differences between the received electric-field strengths and accurately select the predetermined number of top received electric-field strengths from those of the receiving antennas 3a to 3h. By use of the predetermined number of top received electric-field strengths, the position calculator 45a can calculate the data about the position of the capsule endoscope 2 in the subject 1 with high accuracy.

As explained above, in the first embodiment, the capsule endoscope, serving as a transmitting apparatus, wirelessly transmits a modulated signal having a strength detection section containing a carrier signal, which is a narrowband signal component, and a data section containing predetermined data such as in-vivo image data. The receiving device receives modulated signals from the capsule endoscope via the receiving antennas. The receiving device branches the modulated signal as modulated signals to the received-strength detecting system and the signal processing system. The narrowband filter of the received-strength detecting system extracts a narrowband signal component contained in the strength detection section of one of the modulated signals and detects the received electric-field strength of the narrowband signal component. The signal processing system performs the signal processing on the in-vivo image data contained in the data section of the other modulated signal. Therefore, the pass bandwidth of the narrowband filter of the received-strength detecting system can be narrowed depending on the narrowband signal component in the strength detection section. This makes it possible to reduce noise to be input to the received-strength detecting system can be reduced, and detect the received electric-field strength of the narrowband signal component with the approximately fixed signal level. As a result, the lower limit of received electric-field strength detectable by the strength detecting system can be set lower than the received electric-field strengths of the receiving antennas, and the dynamic range of the received electric-field strength can be increased. Accordingly, achieved is a receiving/transmitting system that stably detects a received electric-field strength at which a modulated signal containing predetermined data is received from a transmitting apparatus, and a medical system.

A transmitting/receiving system according to a second embodiment of the present invention is explained below. In the first embodiment, the frequency mixer 33 branches a modulated signal from the capsule endoscope 2. On the other hand, in the second embodiment, an intermediate frequency amplifier 58 branches a modulated signal from the capsule endoscope 2.

Figure 9:
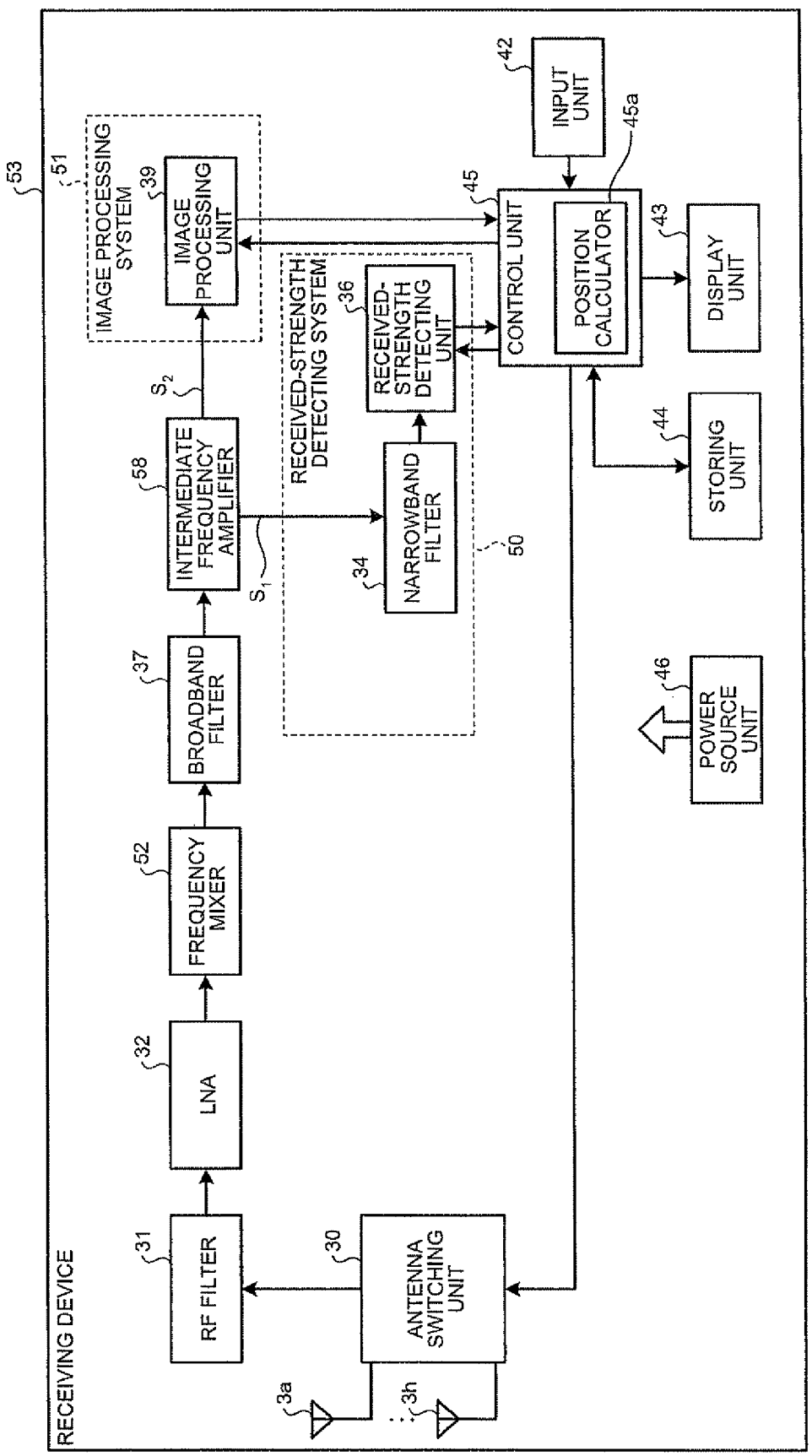
FIG. 9 is a section diagram of a configuration of a receiving device of a transmitting/receiving system according to a second embodiment of the present invention.

FIG. 9 is a section diagram of a configuration of the transmitting/receiving system according to the second embodiment. As shown in FIG. 9, a receiving device 53 of the transmitting/receiving system according to the second embodiment includes a frequency mixer 52 instead of the frequency mixer 33 of the receiving device 3, and includes the intermediate frequency amplifier 58 instead of the intermediate frequency amplifier 38. The receiving device 53 does not include the intermediate frequency amplifier 35 of the received-strength detecting system 40. In the receiving device 53, the narrowband filter 34 and the received-strength detecting unit 36 are connected to each other, and a narrowband signal component extracted by the narrowband filter 34 is input to the received-strength detecting unit 36. In the receiving device 53, a received-strength detecting system 50 includes the narrowband filter 34 and the received-strength detecting unit 36, and an image processing system 51 includes the image processing unit 39. The transmitting/receiving system according to the second embodiment includes the receiving device 53 instead of the receiving device 3 of the transmitting/receiving system according to the first embodiment shown in FIG. 1. Other constituents of the second embodiment are the same as those of the first embodiment, and are denoted by the same reference numerals.

The frequency mixer 52 has the same function as that of the frequency mixer 33 of the receiving device 3 according to the first embodiment except for sending a modulated signal from the capsule endoscope 2 to the broadband filter 37 without branching the modulated signal. In other words, the frequency mixer 52 receives, from the LNA 32, the modulated signal from the capsule endoscope 2, downconverts a high frequency of the modulated signal to an intermediate frequency by mixing the modulated signal with a signal of a different frequency, and outputs the modulated signal to the broadband filter 37 without branching the modulated signal.

The intermediate frequency amplifier 58 has the same function as that of the intermediate frequency amplifier 38 of the receiving device 3 according to the first embodiment except for branching the amplified modulated signal of an intermediate frequency as modulated signals and outputting the modulated signal to the received-strength detecting system 50 and the image processing system 51, respectively. Specifically, after the frequency mixer 52 downconverts the frequency of the modulated signal from the capsule endoscope 2 to the intermediate frequency and passes through the broadband filter 37, the intermediate frequency amplifier 58 amplifies the signal components of the modulated signal, branches the amplified modulated signal as modulated signals, and outputs the modulated signals to the received-strength detecting system 50 and the image processing system 51. A modulated signal $S_1$, which is one of the modulated signals, is sent to the narrowband filter 34 of the received-strength detecting system 50, and a modulated signal $S_2$, which is the other modulated signal, is output to the image processing unit 39 of the image processing system 51.

As explained above, in the second embodiment, the intermediate frequency amplifier, which amplifies the modulated signal from the transmitting apparatus with the frequency having downconverted to the intermediate frequency by the intermediate frequency mixer, is configured to branches the amplified modulated signal as modulated signals and output the modulated signals respectively to the received-strength detecting system and the signal processing system, and other constituents of the second embodiment are the same as those of the first embodiment. Therefore, the same effect as that of the first embodiment can be achieved, and the number of constituents of the received-strength detecting system and the signal processing system of the receiving device can be reduced. Accordingly, the receiving device of the transmitting/receiving system can be achieved with a simple configuration.

A transmitting/receiving system according to a third embodiment of the present invention is explained below. In the first embodiment, the frequency mixer 33 branches a modulated signal from the capsule endoscope 2. On the other hand, in the third embodiment, the LNA 32 branches the modulated signal from the capsule endoscope 2 as modulated signals, and a received-strength detecting system 60 and an image processing system 61 that respectively receive the branched modulated signals include frequency mixers 66 and 67 that downconvert a high frequency of the modulated signal to an intermediate frequency.

Figure 10:
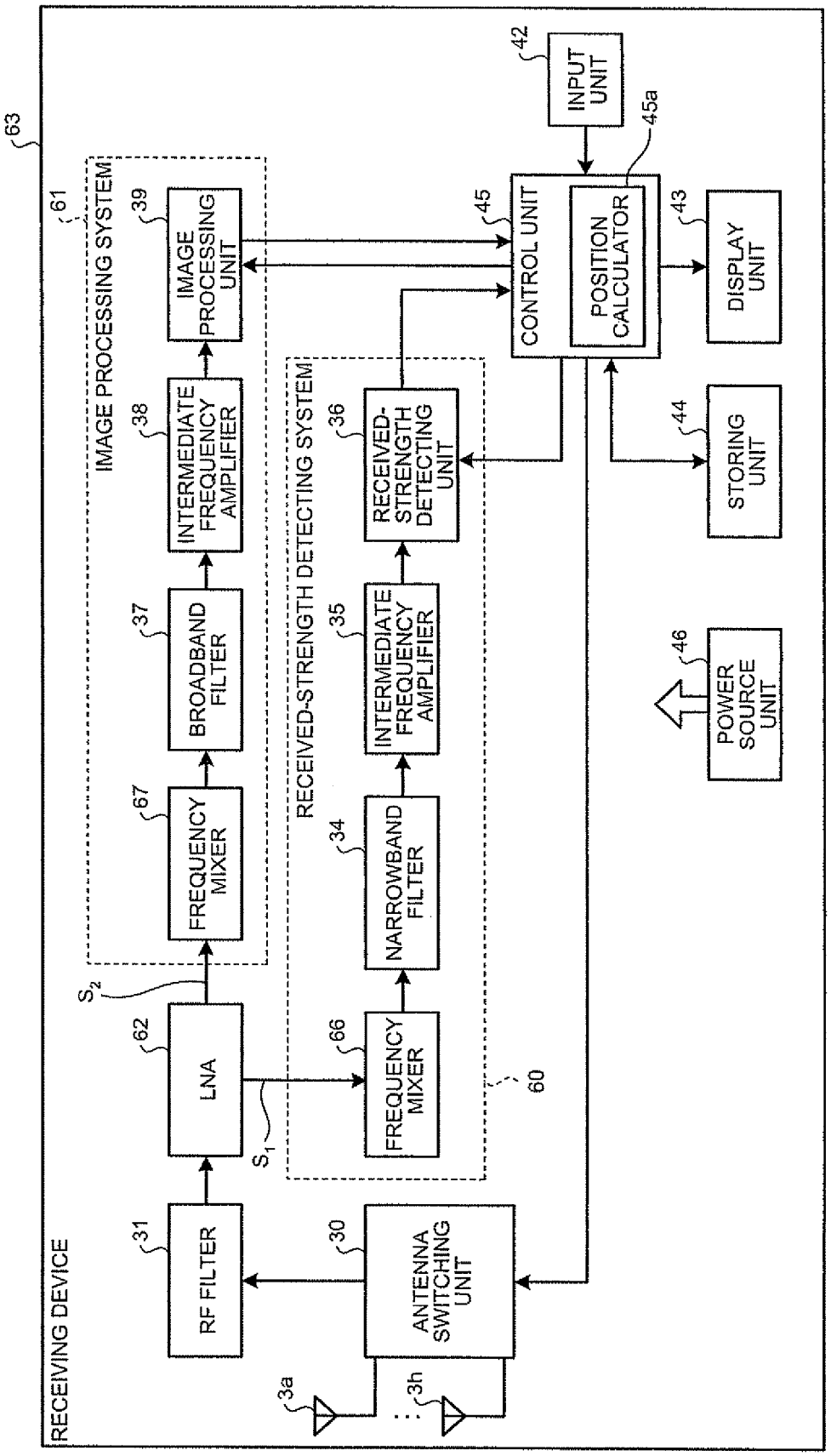
FIG. 10 is a section diagram of a configuration of a receiving device of a transmitting/receiving system according to a third embodiment of the present invention.

FIG. 10 is a section diagram of a configuration of the transmitting/receiving system according to the third embodiment. As shown in FIG. 10, a receiving device 63 of the transmitting/receiving system according to the third embodiment includes an LNA 62 instead of the LNA 32 of the receiving device 3, includes the frequency mixer 67 instead of the frequency mixer 33, and includes the frequency mixer 66 of the received-strength detecting system 60. In the receiving device 63, the received-strength detecting system 60 includes the frequency mixer 66, the narrowband filter 34, the intermediate frequency amplifier 35, and the received-strength detecting unit 36, and the image processing system 61 includes the frequency mixer 67, the broadband filter 37, the intermediate frequency amplifier 38, and the image processing unit 39. The LNA 62 is connected to the frequency mixer 66 of the received-strength detecting system 60 and to the frequency mixer 67 of the image processing system 61. The transmitting/receiving system according to the third embodiment includes the receiving device 63 instead of the receiving device 3 of the transmitting/receiving system according to the first embodiment shown in FIG. 1. Other constituents of the third embodiment are the same as those of the first embodiment, and are denoted by the same reference numerals.

The LNA 62 has the same function as that of the LNA 32 of the receiving device 3 according to the first embodiment except for branching the amplified modulated signal from the capsule endoscope 2 as modulated signals and outputs the modulated signals to the received-strength detecting system 60 and the image processing system 61, respectively. In other words, the LNA 62 amplifies the modulated signal from the capsule endoscope 2 having passed through the RF filter 31, branches the amplified modulated signal as amplified signals, and outputs the amplified signals to the received-strength detecting system 60 and the image processing system 61, respectively. A modulated signal $S_1$, which is one of the modulated signals branched by the LNA 62, is output to the frequency mixer 66 of the received-strength detecting system 60, and a modulated signal $S_2$, which is the other modulated signal, is output to the frequency mixer 67 of the image processing system 61.

The frequency mixer 66 is a frequency mixer of the received-strength detecting system 60 as described above, and it receives the modulated signal $S_1$ branched by the LNA 62 and downconverts the high frequency of the modulated signal $S_1$ to an intermediate frequency by mixing the modulated signal $S_1$ with a signal of a different frequency. The intermediate frequency of the modulated signal $S_1$ obtained by the conversion by the frequency mixer 66 can be easily processed by the received-strength detecting system 60, and it is a favorable frequency for, for example, the received-strength detecting unit 36 to perform processing for detecting a reception eclectic field strength from the modulated signal $S_1$. The frequency mixer 66 sends the downconverted modulated signal $S_1$ to the narrowband filter 34 without branching the downconverted modulated signal $S_1$.

The frequency mixer 67 is a frequency mixer of the image processing system 61 system as described above. The frequency mixer 67 receives the modulated signal $S_2$ branched by the LNA 62, and downconverts the high frequency of the modulated signal $S_2$ to an intermediate frequency by mixing the modulated signal $S_2$ with a signal of a different frequency. The intermediate frequency of the modulated signal $S_2$ obtained by the conversion by the frequency mixer 67 can be easily processed by the image processing system 61, and it is a favorable frequency for, for example, the image processing unit 39 to perform signal processing (image processing) on in-vivo image data D4. The frequency mixer 67 sends the downconverted modulated signal $S_2$ to the broadband filter 37 without branching the downconverted modulated signal $S_2$.

If the intermediate frequency favorable to the received-strength detecting system 60 and the intermediate frequency favorable to the image processing system 61 are not equal, the frequency mixers 66 and 67 can convert the high frequencies of the modulated signals $S_1$ and $S_2$ respectively to different intermediate frequencies (i.e., an intermediate frequency favorable to the received-strength detecting system 60 and an intermediate frequency favorable to the image processing system 61). On the other hand, if the intermediate frequency favorable to the received-strength detecting system 60 and the intermediate frequency favorable to the image processing system 61 are equal, the frequency mixers 66 and 67 can convert the high frequencies of the modulated signals $S_1$ and $S_2$ respectively to equal intermediate frequencies.

As explained above, in the third embodiment, the received-strength detecting system and the signal processing system of the receiving device respectively include the frequency mixers each configured to downconvert a high frequency of a modulated signal to an intermediate frequency. The LNA, which amplifies the modulated signal from the transmitting apparatus having passed through the RF filter, branches the modulated signal as modulated signals and outputs the modulated signals to the received-strength detecting system and the signal processing system. The frequency mixer of the received-strength detecting system converts the high frequency of one of the modulated signals, the frequency mixer of the signal processing system converts the high frequency of the other modulated signal, and other constituents of the third embodiment are same as those of the first embodiment. Therefore, the same effects as that of the first embodiment can be achieved. In addition, even when the intermediate frequency favorable to the received-strength detecting system and the intermediate frequency favorable to the image processing system are not equal, the intermediate frequency of the modulated signal input to the received-strength detecting system can be converted to a frequency to be easily processed by the received-strength detecting system, and the intermediate frequency of the modulated signal input to the image processing system can be converted to a frequency to be easily processed by the signal processing system.

A transmitting/receiving system according to a fourth embodiment of the present invention is explained below. In the first embodiment, only the narrowband signal component having the carrier frequency, i.e., the unmodulated carrier signal, is contained in the strength detection section A of the modulated signal to be wirelessly exchanged between the capsule endoscope 2 and the receiving device 3. On the other hand, in the fourth embodiment, a modulated signal containing, in the strength detection section A2, at least a plurality of narrowband signal components including a carrier frequency component is wirelessly exchanged between a capsule endoscope 72 and a receiving device 83, and an electric field strength of any one of the narrowband signal components contained in the strength detection section A2 is detected.

Figure 11:
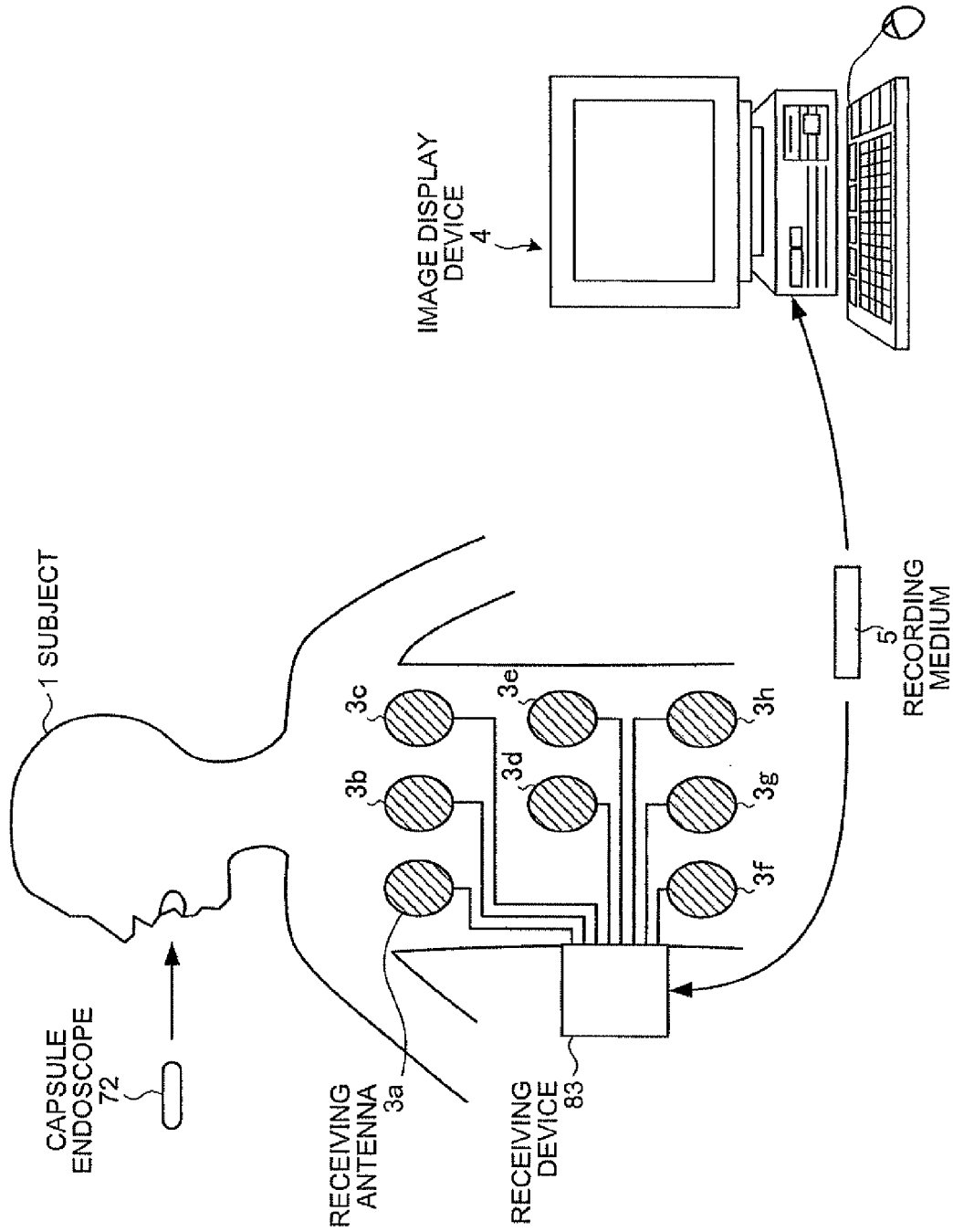
FIG. 11 is a schematic diagram of a configuration of a transmitting/receiving system according to a fourth embodiment of the present invention.

FIG. 11 is a schematic diagram of a configuration of the transmitting/receiving system according to the fourth embodiment. As shown in FIG. 11, the transmitting/receiving system according to the fourth embodiment includes the capsule endoscope 72 instead of the capsule endoscope 2 of the transmitting/receiving system according to the first embodiment shown in FIG. 1, and includes the receiving device 83 instead of the receiving device 3. Other constituents are the same as those of the first embodiment, and are denoted by the same reference numerals.

The capsule endoscope, which serves as a transmitting apparatus, has the same function as that of the capsule endoscope 2 according to the first embodiment except that the signal formats of a transmission signal and a modulated signal containing in-vivo image data about the subject 1 are different from those of the first embodiment.

The receiving device 83 receives a modulated signal wirelessly transmitted from the capsule endoscope 72. The receiving device 83 has the same function as that of the receiving device 3 according to the first embodiment except that the timing at which in-vivo image data contained in a modulated signal is different from that of the first embodiment.

Figure 12:
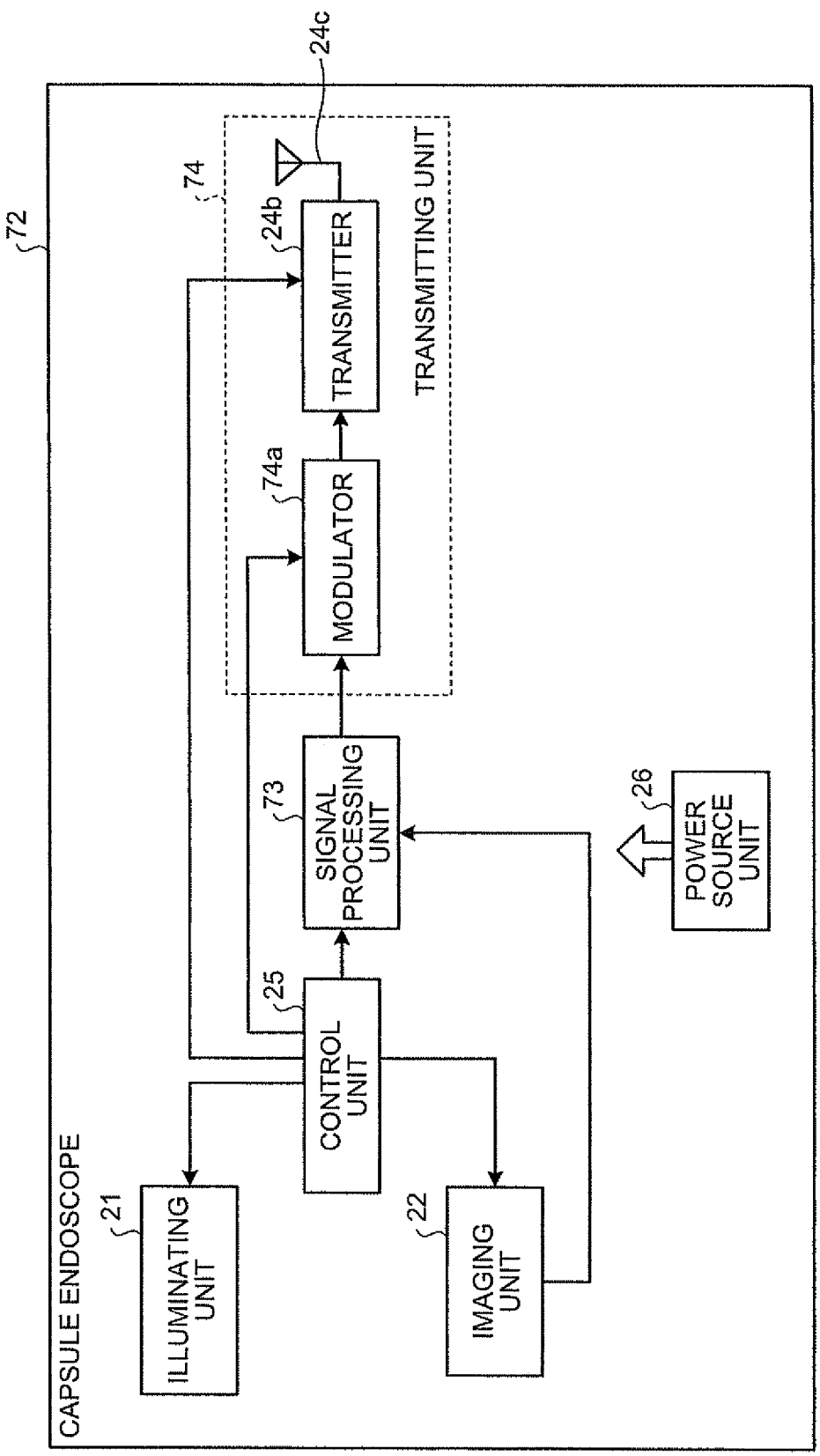
FIG. 12 is a section diagram of a configuration of a capsule endoscope, which serves as a transmitting apparatus, according to the fourth embodiment of the present invention.

The configuration of the capsule endoscope 72 according to the fourth embodiment is explained in detail below. FIG. 12 is a section diagram of the configuration of the capsule endoscope 72. As shown in FIG. 12, the capsule endoscope 72 includes a signal processing unit 73 instead of the signal processing unit 23 of the capsule endoscope 2 according to the first embodiment, and includes a transmitting unit 74 instead of the transmitting unit 24. The transmitting unit 74 includes a modulator 74a instead of the modulator 24a of the capsule endoscope 2 according to the first embodiment. Other constituents are the same as those of the first embodiment, and are denoted by the same reference numerals.

The signal processing unit 73 functions as a signal generating unit that generates a transmission signal to be wirelessly transmitted from the capsule endoscope 72 to the receiving device 83. The signal processing unit 73 operates under the control by the control unit 25. Each time when the imaging unit 22 captures an image, the signal processing unit 73 receives in-vivo image data from the imaging unit 22, and generates a transmission signal containing the in-vivo image data. Specifically, the signal processing unit 73 generates a one-frame transmission signal S10 containing one-frame in-vivo image data based on the signal format shown in FIG. 13. In other words, the signal processing unit 73 assigns a detection signal containing detection data D1 for signal detection to a signal detection section A1, which is the top signal section of the transmission signal $S_{10}$, assigns a digital signal containing digital data D12 with a predetermined fixed repetition cycle to an strength detection section A2 subsequent to the signal detection section A1, and assigns an image signal containing in-vivo image data D4 received from the imaging unit 22 to a data section A4 subsequent to the strength detection section A2, so that the one-frame transmission signal $S_{10}$ is generated. The signal processing unit 73 transmits the transmission signal $S_{10}$ to the transmission unit 24.

The digital signal in the strength detection section A2, which is an example of a specific signal whose frequency is fixed to a predetermined value other than zero, consists of the digital data D12 in which a digital value (1) and a digital value (0) are alternately repeated in the predetermined cycle (i.e., fixed digital data of fixed data pattern in which the digital value (1) and the digital value (0) are alternately repeated). The signal processing unit 73 fixes the frequency of the digital signal consisting of the digital data D12 to a frequency twice a frequency deviation $\Delta f_c$ corresponding to a carrier frequency $f_c$ of the modulator 74a, and assigns the digital signal of the fixed frequency (=2·$\Delta f_c$), i.e., the digital data D12, to the strength detection section A2.

The frequency (=2·$\Delta f_c$) of the digital signal assigned to the strength detection section A2 of the transmission signal $S_{10}$ by the signal processing unit 73 is calculated based on the following Equation (1):

$$2 \cdot \Delta f_c = f_b \cdot m \quad (1)$$

where $f_b$ is a maximum transmission rate [bps] at which the digital signal in the strength detection section A2 is input to the modulator 74a, and m is a modulation index of the modulator 74a.

The signal processing unit 73 assigns, to the strength detection section A2 of the transmission signal S10, the digital signal with the frequency fixed to the value obtained by multiplying the maximum transmission rate $f_b$ with the modulation index m. For example, when the maximum transmission rate $f_b$ is 4 Mbps and the modulation index m is 0.5, the signal processing unit 73 assigns the digital signal whose frequency is fixed to 2 MHz to the strength detection section A2 of the transmission signal $S_{10}$.

The transmitting unit 74 performs digital modulation (specifically, minimum shift keying (MSK)) on the transmission signal $S_{10}$ generated by the signal processing unit 73, and wirelessly transmits the modulated transmission signal to the outside. The transmitting unit 74 includes the modulator 74a that performs MSK on the transmission signal $S_{10}$ generated by the signal processing unit 73, and the transmitter 24b that wirelessly transmits the transmission signal $S_{10}$ modulated by the modulator 74a to the outside.

The modulator 74a performs MSK on the transmission signal $S_{10}$ generated by the signal processing unit 73, and generates a modulated signal containing, in the strength detection section A2, the narrowband signal components including the carrier signal component. Specifically, the modulator 74a includes a signal sending unit that sends a carrier signal of a carrier frequency $f_c$ and a voltage controlled oscillator (VCO), and the modulation index is set to 0.5. Under the control by the control unit 25, the modulator 74a receives the transmission signal $S_{10}$ from the signal processing unit 73. Each time when the modulator 74a receives a transmission signal, the modulator 74a performs MSK by overlaying the transmission signal $S_{10}$ and the carrier signal. While performing PLL control for fixing the frequency to the carrier frequency $f_c$, the modulator 74a generates a modulated signal by performing MSK on the transmission signal $S_{10}$.

The modulated signal generated by the modulator 74a contains a broadband signal component corresponding to the detection data D1 in the signal detection section A1, contains the narrowband signal component corresponding to the digital signal containing the digital data D12 in the strength detection section A2, and contains a broadband signal component corresponding to the in-vivo image data D4 in the data section A4. When the digital signal in the strength detection section A2 is a digital signal whose frequency is fixed to a frequency twice the frequency deviation $\Delta f_c$ the modulated signal obtained by performing MSK on the digital signal in the strength detection section A2 contains a plurality of narrowband signal components including at least the carrier frequency component. By performing MSK on the transmission signal $S_{10}$, the modulator 74a generates the modulated signal containing, in the strength detection section A2, the narrow signal components including at least the carrier frequency component.

As shown in FIG. 14, the frequency characteristics of the modulated signal in the strength detection section A2 are that a frequency spectrum rises at each of the carrier frequency $f_c$, a frequency $f_0$ corresponding to the digital value (0), a frequency $f_1$ corresponding to the digital value (1), a frequency that shifts from the frequency $f_0$ by $2 \cdot \Delta f_c$ to the lower frequency side, and a frequency that shifts from the frequency $f_1$ by $2 \cdot \Delta f_c$ to the higher frequency side. In other words, the narrowband signal component with the frequency spectrum at the carrier frequency $f_c$, the narrowband signal component with the frequency spectrum at the frequency $f_o$, the narrowband signal component with the frequency spectrum at the frequency that shifts from the frequency $f_o$ by $2 \cdot \Delta f_c$ to the lower frequency side, and the narrowband signal component with the frequency spectrum at the frequency that shifts from the frequency $f_1$ by $2 \cdot \Delta f_c$ to the higher frequency side are diversely contained in the strength detection section A2 of the modulated signal. The bandwidth of each narrowband signal component contained in the strength detection section A2 is, for example, about several tens of kHz.

The modulator 74a sends the modulated signal generated by MSK to the transmitter 24b. The transmitter 24b wirelessly transmits the modulated signal received from the modulator 74a to the receiving device 83 via the transmitting antenna 24c.

Figure 15:
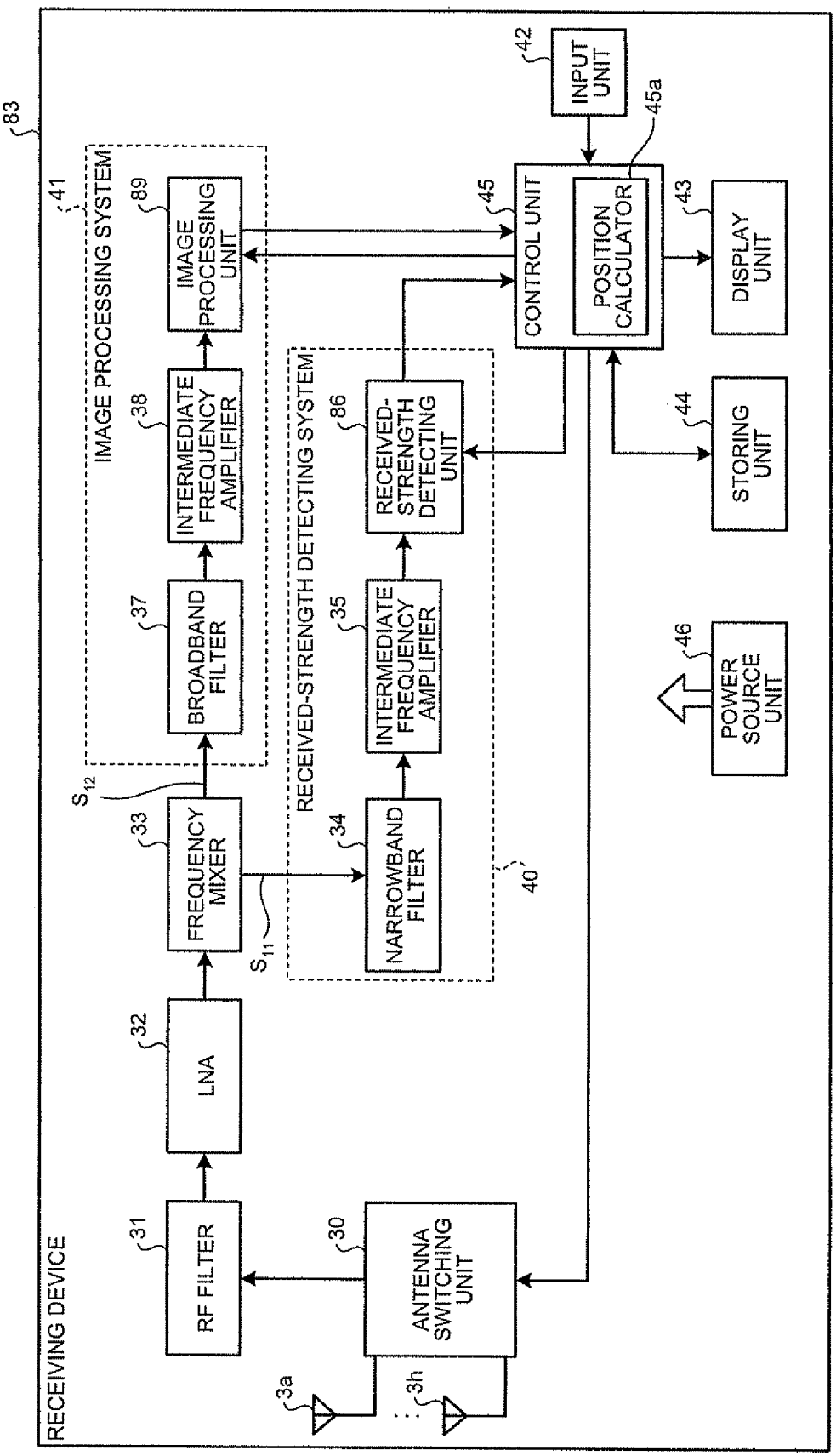
FIG. 15 is a section diagram of a configuration of a receiving device according to the fourth embodiment.

The configuration of the receiving device 83 is explained in detail below. FIG. 15 is a section diagram of the configuration of the receiving device 83 according to the fourth embodiment of the present invention. As shown in FIG. 15, the receiving device 83 includes a received-strength detecting unit 86 instead of the received-strength detecting unit 36 of the receiving device 3 according to the first embodiment, and includes an image processing unit 89 instead of the image processing unit 39. In the receiving device 83, the received-strength detecting system 40 includes the narrowband filter 34, the intermediate frequency amplifier 35, and the received-strength detecting unit 86, and the image processing system 41 includes the broadband filter 37, the intermediate frequency amplifier 38, and the image processing unit 89. In the fourth embodiment, the frequency mixer 33 downconverts the high frequency of the modulated signal obtained by performing MSK on the transmission signal $S_{10}$ shown in FIG. 13 to an intermediate frequency, branches the downconverted modulated signal as modulated signals, and outputs the modulated signals to the received-strength detecting system 40 and the image processing system 41. A modulated signal $S_{11}$, which is one of the modulated signals branched by the frequency mixer 33, is input to the received-strength detecting system 40, and a modulated signal $S_{12}$, which is the other modulated signal, is input to the image processing system 41. Other constituents are same as those of the first embodiment, and are denoted by the same reference numerals.

The received-strength detecting unit 86 has a function of detecting a received electric-field strength as the received-strength detecting unit 36 of the receiving device 3 according to the first embodiment does, and detects a received electric-field strength of a narrowband signal component extracted by the narrowband filer 34 from the narrowband signal components contained in the strength detection section A2 of the modulated signal $S_{11}$. It is desirable that the narrowband filter 34 extracts a narrowband signal component of the carrier frequency from the narrowband signal components in the strength detection section A2, i.e., extracts the carrier signal with the highest and stable signal level among the narrowband signal components, and that the received-strength detecting unit 86 detects a received electric-field strength of the carrier signal extracted by the narrowband filter 34. The received electric-field strength detected by the received-strength detecting unit 86 is sent to the control unit 45 as in the case of the first embodiment.

The image processing unit 89 generates an in-vivo image of the subject 1 by performing signal processing on the in-vivo image data D4 contained in the data section A4 of the modulated signal S12. The image processing unit 89 has the same signal processing function as that of the image processing unit 39 of the receiving device 3 according to the first embodiment except that the timing at which the signal processing is performed on the in-vivo image data D4 after receiving an instruction for starting operation from the control unit 45 is different from that of the image processing unit 39. The in-vivo image of the subject 1 generated by the image processing unit 89 is sent to the control unit 45 as in the case of the first embodiment.

Figure 16:
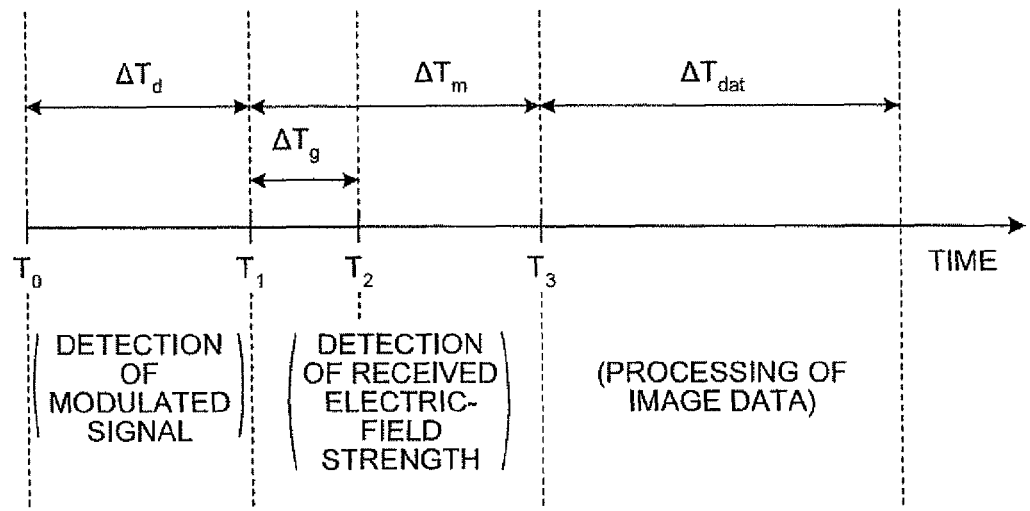
FIG. 16 is a schematic diagram of operation timing of the receiving device according to the fourth embodiment.

The operations of the received-strength detecting unit 86 and the image processing unit 89 of the receiving device 83 according to the fourth embodiment are explained below. FIG. 16 is a schematic diagram of the operation timing of the receiving device 83. Explained below with reference to FIG. 16 is the operation of the receiving device 83 for detecting the received electric-field strength of the one-frame modulated signal obtained by performing MSK on the one-frame transmission signal $S_{10}$, and for performing the signal processing on the in-vivo image data.

The receiving device 83 receives the modulated signal from the capsule endoscope 72 via the receiving antenna selected from the receiving antennas 3a to 3h by the antenna switching unit 30, and the frequency mixer 33 branches the modulated signal as the modulated signals $S_{11}$ and $S_{12}$. The control unit 45 causes the received-strength detecting unit 86 and the image processing unit 89 to start the operation at the timing (time $T_0$) at which the control unit 45 causes the antenna switching unit 30 to select the receiving antenna.

The image processing unit 89 starts the operation under the control by the control unit 45, and detects that the one-frame modulated signal is wirelessly transmitted from the capsule endoscope 72 from the time $T_0$ until a signal detection period $\Delta T_d$ passes. The image processing unit 89 receives the broadband signal component in the signal detection section A1 of the modulated signal S12 having passed through the broadband filter 37, and detects the start of the modulated signal S12 based on the detection data D1 contained in the broadband signal component.

The received-strength detecting unit 86 detects the received electric-field strength of the modulated signal $S_{11}$, i.e., the received electric-field strength of each receiving antenna, from the timing (time $T_1$) at which the signal detection period $\Delta T_d$ passes until an strength detection period $\Delta T_m$ passes. Specifically, the received-strength detecting unit 86 waits to start the processing for detecting the received electric-field strength for a period from the time $T_1$ until a guard period $\Delta T_g$ passes, and starts the processing for detecting the received electric-field strength at the timing (time $T_2$) at which the guard period $\Delta T_g$ passes. In the strength detection period $T_m$, the received-strength detecting unit 86 detects the received electric-field strength of one of the narrowband signal components contained in the strength detection section A2, such as the carrier signal. The electric field strength of the narrowband signal component detected by the received-strength detecting unit 86 is sent to the control unit 45 as the result of the electric field strength detection on a per receiving-antenna basis.

On the other hand, the image processing unit 89 performs the signal processing on the in-vivo image data D4 contained in the data section A4 of the modulated signal $S_{12}$ from the timing (time $T_3$) at which the strength detection period $\Delta T_m$ passes until a data processing period $\Delta T_{dat}$ passes. In other words, in the data processing period $\Delta T_{dat}$, the image processing unit 89 receives the one-frame in-vivo image data D4 and generates the one-frame in-vivo image based on the in-vivo image data D4. The image processing unit 89 sends the one-frame in-vivo image, i.e., the in-vivo image of the subject 1, to the control unit 45.

Thereafter, the image processing unit 89 enters a wait state until the control unit 45 gives an instruction for stating the operation to the image processing unit 89. In the data processing period $\Delta T_{dat}$, while receiving the modulated signal $S_{11}$, the received-strength detecting unit 86 waits to start the processing for detecting the received electric-field strength, and continues the wait state until the control unit 45 gives an instruction for starting the operation to the received-strength detecting unit 86. Each time when the control unit 45 gives the instruction for starting the operation, the received-strength detecting unit 86 and the image processing unit 89 repeatedly performs the operations described above according to the operation timing shown in FIG. 16. As a result, the received-strength detecting unit 86 sequentially detects the received electric-field strengths of the receiving antennas and the image processing unit 39 sequentially generates one-frame in-vivo images.

As shown in FIG. 13, the digital signal including the digital data D12 with the fixed data pattern is assigned to the strength detection section A2 of the transmission signal $S_{10}$ from the capsule endoscope 72. Therefore, to the strength detection section A2 of the modulated signal (i.e., the modulated signals $S_{11}$ and $S_{12}$) obtained by performing MSK on the transmission signal $S_{10}$, the signal components with the frequency characteristics shown in FIG. 14 in which the frequency is changed are assigned. The modulated signal contains, in the strength detection section A2, the narrowband signal components including at least the carrier frequency component. Therefore, in each of the transmission signal $S_{10}$ and the modulated signals $S_{11}$ and $S_{12}$, the level of the frequency can be can smoothly shift from that of the strength detection section A2 to that of the data section A4 without setting the idling section A3 between the strength detection section A2 and the data section A4. As a result, after the strength detection period $\Delta T_m$ the image processing unit 89 can obtain the stable in-vivo image data in the data processing period $\Delta T_{dat}$ without the idling period $\Delta T_i$. Accordingly, the image processing unit 89 can perform the image processing on the in-vivo image data in a period shorter than that required in the first embodiment.

As explained above, in the fourth embodiment, the digital signal consisting of the digital data with the fixed data pattern is assigned to the strength detection section of the transmission signal, the modulated signal obtained by performing MSK on the transmission signal is exchanged by wireless communication, and other constituents are same as those of the first embodiment. Therefore, the same effect as that of the first embodiments can be achieved. In addition, without setting the idling section between the strength detection section and the data section of the modulated signal, the stable data (for example, image data) can be received in the data processing period of the signal processing system. This shortens the time required before the data in the modulated signal is processed.

Figure 17:
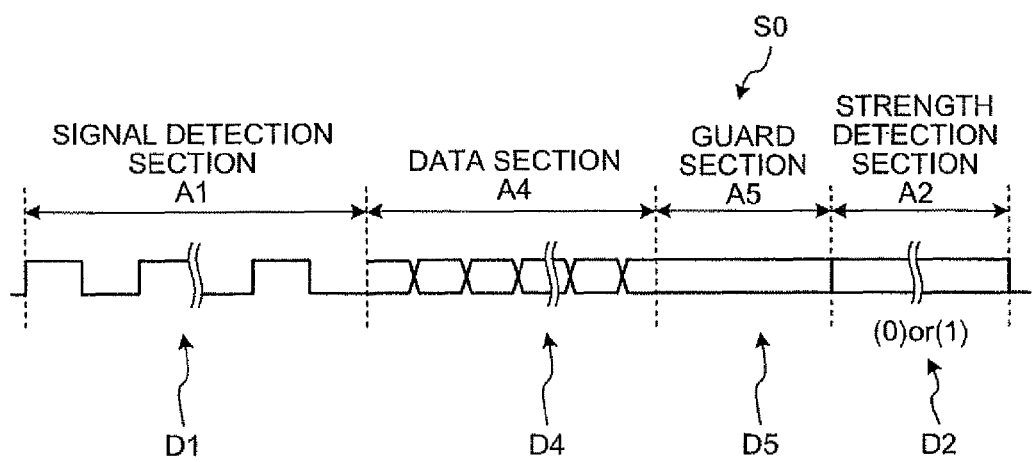
FIG. 17 is a schematic diagram of a modified example of the signal format of the transmission signal from the capsule endoscope.

In the first to fourth embodiments, the strength detection section A2 is set before the data section A4 in the signal format. Alternatively, the strength detection section A2 can be set after the data section A4. Specifically, as a transmission signal $S_0$ shown in FIG. 17, the signal processing unit 23 of the capsule endoscope 2 according to each of the first to third embodiments can set the signal detection section A1 containing the detection data D1 as a top signal section, set the data section A4 containing the in-vivo image data D4 as a signal section subsequent to the signal detection section A1, set the guard section A5 as a signal section subsequent to the data section A4, and set the strength detection section A2 containing the fixed digital data D2 as a signal section subsequent to the guard section A5. The guard section A5 is a signal section that cancels instability of the frequency caused along the shift of the signal component from that in the data section A4 to that in the strength detection section A2, and the guard section A5 contains the fixed digital data D5 having the same digital value as that of the strength detection section A2 (0 or 1). Because the signal processing unit 73 of the capsule endoscope 72 according to the fourth embodiment assigns the digital data 12 having the fixed data pattern in the strength detection section A2 of the transmission signal, the strength detection section A2 can be set as a signal section subsequent to the data section A4 without setting the guard section A5.

If the strength detection section A2 is set after the data section A4, it suffices that the received-strength detecting unit and the image processing unit of the receiving device according to each of the first to fourth embodiments appropriately sets operation periods (the signal detection period $\Delta T_d$, the guard period $\Delta T_g$, the strength detection period $\Delta T_g$, the data processing period $T_{dat}$, and the idling period $\Delta T_i$) corresponding to the signal format, and performs the processing for detecting an electric-field strength and signal processing on in-vivo image data according to the set operation periods.

In addition, in the first to fourth embodiments, the receiving device calculates (detects) data about the position of the capsule endoscope. Alternatively, the image display device 4 of the system (transmitting/receiving or medical system) can be configured to calculate the data about the position of the capsule endoscope. In this case, the receiving device stores the received electric-field strength of each receiving antenna in association with an in-vivo image in, for example, the recording medium, and the image display device 4 reads the received electric-field strength and the in-vivo image and calculates the data about the position of the capsule endoscope using the electric field strength.

Furthermore, in the first to fourth embodiments, the capsule endoscope 2 is explained as a transmitting apparatus. Alternatively, a capsule medical apparatus that acquires various types of in-vivo data including the pH and temperature as predetermined data and wirelessly transmits the in-vivo data can be used. Alternatively, other various types of transmitting apparatuses (other than medical apparatuses) that wirelessly transmit predetermined data other than in-vivo data can be used. The predetermined data to be exchanged between the transmitting apparatus and the receiving device of the receiving/transmitting system is not limited to the in-vivo image data, and other arbitral data can be exchanged. In other words, the image processing system of the receiving device can be a signal processing system that performs the signal processing on the arbitral data.

In the first to fourth embodiments, the position detection processing in which the data about the position of the capsule endoscope in the subject is calculated is performed as an application using the received electric-field strength of each receiving antenna. Alternatively, a desired application in which electric field intensities of a desired number of receiving antennas are used can be employed.

In the first to third embodiments, the modulator 24a of the capsule endoscope 2 performs the FSK on the transmission signal $S_0$ generated by the signal processing unit 23. Alternatively, the modulator 24a can modulate the transmission signal $S_0$ by performing a digital modulation other than the FSK (for example, amplitude shift keying (ASK), phase shift keying (PSK), or quadrature amplitude modulation (QAK)).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical system comprising:
   a wireless transmitting medical apparatus including a transmitting unit that generates a modulated signal containing a broadband signal component and a narrowband signal component, and that transmits the modulated signal to the outside the wireless medical apparatus; and
   a receiving device that receives the modulated signal via at least three receiving antennas, the receiving device including
      a signal processing system that processes the broadband signal component contained in the modulated signal; and
      a received-strength detecting system that processes the narrowband signal component contained in the modulated signal,
   wherein data about the narrowband signal component processed by the received-strength detecting system is used to detect a position of the wireless transmitting medical apparatus;
   the wireless transmitting medical apparatus includes
      a signal processing unit that generates a transmission signal having a signal section containing a specific signal with a fixed frequency and a data section containing in-vivo data about a subject; and
      a modulator that performs digital modulation on the transmission signal, and generates the modulated signal containing the narrowband signal component corresponding to the specific signal in the signal section;
   the signal processing unit generates the transmission signal containing the specific signal that is a direct current signal in the signal section and the in-vivo data in the data section, and
   the modulator performs the digital modulation on the transmission signal generated by the signal processing unit, and generates the modulated signal containing the narrowband signal component that is a carrier frequency component in the signal section.

2. The medical system according to claim 1, wherein the in-vivo data is in-vivo image data about the subject, the wireless transmitting medical apparatus is a capsule medical apparatus to be introduced into the subject, and the capsule medical apparatus is a capsule endoscope including an imaging unit that captures the in-vivo image data about the subject.

3. The medical system according to claim 1, wherein the receiving device branches the modulated signal as modulated signals to the received-strength detecting system and the signal processing system,
   the received-strength detecting system includes a narrowband filter that extracts the narrowband signal component contained in the signal section of one of the modulated signals,
   the received-strength detecting system detects a received electric-field strength that is the data about the narrowband signal component,
   the signal processing system includes a broadband filter that extracts the broadband signal component contained in the data section of the other modulated signal, and
   the signal processing system performs signal processing on data contained in the broadband signal component.

4. The medical system according to claim 3, wherein the receiving device includes a broadband filter that has a pass bandwidth approximately equal to an occupied bandwidth of the modulated signal, and
   the narrowband filter has a pass bandwidth not smaller than one-ten-thousandth of the pass bandwidth of the broadband filter and not larger than one-tenth of the pass bandwidth of the broadband filter.

5. The medical system according to claim 3, wherein the receiving device includes a frequency mixer that converts a frequency of the modulated signal to an intermediate frequency by mixing the modified signal with a signal of a different frequency, and that branches the modulated signal as modulated signals to the received-strength detecting system and the signal processing system.

6. The medical system according to claim 3, wherein the receiving device includes
   a frequency mixer that converts a frequency of the modulated signal to an intermediate frequency by mixing the modulated signal with a signal of a different frequency; and
   an intermediate frequency amplifier that amplifies the modulated signal whose frequency is converted by the frequency mixer, and branches the modulated signal amplified by the intermediate frequency amplifier as modulated signals to the received-strength detecting system and the signal processing system.

7. The medical system according to claim 3, wherein the receiving device includes an amplifier that amplifies the modulated signal, and branches the modulated signal amplified by the amplifier as modulated signals to the received-strength detecting system and the signal processing system,
   the received-strength detecting system includes
   a first frequency mixer that converts a frequency of one of the modulated signals branched by the amplifier to an intermediate frequency by mixing the modulated signal with a signal of a different frequency, and that outputs the modulated signal whose frequency is converted by the frequency mixer to the narrowband filter; and
   a second frequency mixer that converts a frequency of the other modulated signal to an intermediate frequency by mixing the modulated signal with a signal of a different frequency, and that outputs the modulated signal whose frequency is converted by the frequency mixer to the broadband filter.

8. The medical system according to claim 1, wherein the signal processing unit generates the transmission signal that has an idling section subsequent to the signal section, the idling section containing a digital signal in which high-level digital data and low-level digital data are repeated, and that has the data section subsequent to the idling section.

9. The medical system according to claim 1, wherein the signal processing unit generates the transmission signal that has a guard section subsequent to the data section and containing the direct current signal, which is the specific signal, and that has the signal section subsequent to the guard section.

10. The medical system according to claim 1, wherein the received-strength detecting system detects a received electric-field strength of the narrowband signal component at timing after a period in which the signal processing system detects a start of the modulated signal passes.

11. The medical system according to claim 1, wherein the signal processing system processes the broadband signal component and the received-strength detecting system processes the narrowband signal component based on a time sharing system.

* * * * *